(12) United States Patent
Sato et al.

(10) Patent No.: US 12,420,090 B2
(45) Date of Patent: Sep. 23, 2025

(54) METHOD OF CONTROLLING MOVEMENT OF HYBRID ROBOT AND ANIMAL LOCOMOTION STIMULATION SYSTEM THEREOF

(71) Applicants: NANYANG TECHNOLOGICAL UNIVERSITY, Singapore (SG); KLASS ENGINEERING & SOLUTIONS PTE LTD, Singapore (SG)

(72) Inventors: Hirotaka Sato, Singapore (SG); Huu Duoc Nguyen, Singapore (SG); Feng Cao, Singapore (SG); Doan Tat Thang Vo, Singapore (SG); Hee Chuan Seah, Singapore (SG); Bing Hui Terence Goh, Singapore (SG); Sook Fuen Wong, Singapore (SG)

(73) Assignees: Nanyang Technological University, Singapore (SG); KLASS Engineering & Solutions Pte Ltd, Singapore (SG)

( * ) Notice: Subject to any disclaimer, the term of this patent is extended or adjusted under 35 U.S.C. 154(b) by 577 days.

(21) Appl. No.: 17/780,952

(22) PCT Filed: Nov. 27, 2020

(86) PCT No.: PCT/SG2020/050702
§ 371 (c)(1),
(2) Date: May 27, 2022

(87) PCT Pub. No.: WO2021/107883
PCT Pub. Date: Jun. 3, 2021

(65) Prior Publication Data
US 2023/0001198 A1    Jan. 5, 2023

(30) Foreign Application Priority Data
Nov. 29, 2019    (SG) .......................... 10201911368Y

(51) Int. Cl.
*A61N 1/36* (2006.01)
*A01K 29/00* (2006.01)
*A61F 2/70* (2006.01)

(52) U.S. Cl.
CPC .......... *A61N 1/36003* (2013.01); *A01K 29/00* (2013.01); *A61F 2002/704* (2013.01); *A61H 2201/5079* (2013.01)

(58) Field of Classification Search
CPC ....................... G05D 1/0088; A61F 2002/704; G06N 3/061; A01K 15/021; A01K 1/031
See application file for complete search history.

(56) References Cited

U.S. PATENT DOCUMENTS

| | | | |
|---|---|---|---|
| 8,634,635 B2 * | 1/2014 | Bai .................. | A01K 1/031 382/154 |
| 10,959,398 B1 * | 3/2021 | Betts-Lacroix ...... | G06V 10/143 |

(Continued)

FOREIGN PATENT DOCUMENTS

| | | |
|---|---|---|
| CN | 101467515 A | 7/2009 |
| CN | 104199461 A | 12/2014 |

(Continued)

OTHER PUBLICATIONS

Extended European Search Report, dated Nov. 2, 2023, for European Patent Application No. 20891943.1. (8 pages).

(Continued)

*Primary Examiner* — Mirza F Alam
(74) *Attorney, Agent, or Firm* — Seed IP Law Group LLP

(57) ABSTRACT

A method of controlling a movement of a hybrid robot including a locomotion stimulation device carried by an animal includes monitoring, via a positioning component the locomotion stimulation device, a position and an orientation of the hybrid robot; providing, via a stimulator of the locomotion stimulation device, a stimulus to the animal (Continued)

based on an angular difference between the orientation with respect to a direct path from the position to a predetermined destination to control the movement of the hybrid robot; monitoring, via the positioning component, one or a combination of a displacement, a velocity or an acceleration of the hybrid robot in response to the stimulus; ceasing provision of the stimulus to the animal in response to the one or the combination of the displacement, the velocity or the acceleration being below a corresponding pre-defined minimum so as to allow the animal to roam freely.

20 Claims, 5 Drawing Sheets

(56) References Cited

U.S. PATENT DOCUMENTS

| | | | |
|---|---|---|---|
| 2003/0199944 A1* | 10/2003 | Chapin | G06N 3/061 607/48 |
| 2010/0025527 A1 | 2/2010 | Lal et al. | |
| 2012/0189549 A1* | 7/2012 | Claridge-Chang | A01K 29/005 600/300 |

FOREIGN PATENT DOCUMENTS

| | | |
|---|---|---|
| CN | 104199461 B | 2/2017 |
| CN | 108127662 A | 6/2018 |

OTHER PUBLICATIONS

Nguyen et al., "Ultra-Lightweight Cyborg Insect: Sideways walking of remote-controlled living beetle with a miniature backpack," 2019 IEEE International Conference on Cyborg and Bionic Systems, Munich, Germany, Sep. 19-20, 2019, p. 11-16.

Kosowatz, "Biobots to the Rescue," ASME.org, Jan. 12, 2017, URL=https://www.asme.org/topics-resources/content/biobots-to-the-rescue, download date Mar. 11, 2021. (5 pages).

Moore et al., "Directed Locomotion in Cockroaches: 'Biobots'," *Acta entomologica slovenica* 6(2):71-78, Dec. 1998.

Office Action, with English translation, dated Aug. 27, 2024, for Japanese Patent Application No. 2022-530956. (6 pages).

* cited by examiner

METHOD OF CONTROLLING MOVEMENT OF HYBRID ROBOT AND ANIMAL LOCOMOTION STIMULATION SYSTEM THEREOF

CROSS-REFERENCE TO RELATED APPLICATIONS

The present application claims the benefit of the Singapore patent application No. 10201911368Y filed on 29 Nov. 2019, the entire contents of which are incorporated herein by reference for all purposes.

TECHNICAL FIELD

Various embodiments generally relate to a method of controlling a movement of a hybrid robot and an animal locomotion stimulation system for controlling a movement of a hybrid robot. In particular, various embodiments generally relate to a method of controlling a movement of a hybrid robot having a locomotion stimulation device carried by an animal, and an animal locomotion stimulation system for controlling a movement of a hybrid robot using an animal as a legged platform.

BACKGROUND

Man-made small-legged robots are portable, inconspicuous, and some of them are even able to pass through tiny openings and narrow corridors. This makes them excellent choices for a wide range of tasks and operations, such as scouts in search and rescue missions in disaster-hit areas and clandestine vehicles that can be used for environmental monitoring. However, even state-of-the-art man-made legged robots have problems with power consumption and controllability. Power consumption is typically a critical issue for such man-made legged robot as the power consumptions are usually in the order of 1,000 mW. Further, it is also very difficult for man-made legged robots to traverse obstacles that are in their walking pathways. Though extensive efforts have been made to develop legged robots that can climb a variety of surfaces, such complex manoeuvres generally also increase the power consumptions.

Accordingly, there is a need for a more efficient solution to address the above issues.

SUMMARY

According to various embodiments, there is provided a method of controlling a movement of a hybrid robot including a locomotion stimulation device carried by an animal. The method including monitoring, via a positioning component of an electronic backpack of the locomotion stimulation device of the hybrid robot, a position and an orientation of the electronic backpack of the locomotion stimulation device as a measure of a position and an orientation of the hybrid robot. The method including providing, via a stimulator of the electronic backpack of the locomotion stimulation device, a stimulus to the animal based on an angular difference between the orientation of the electronic backpack of the locomotion stimulation device with respect to a direct path from the position of the electronic backpack to a predetermined destination for stimulating the animal to move in a desired manner so as to control the movement of the hybrid robot. The method including monitoring, via the positioning component of the electronic backpack of the locomotion stimulation device of the hybrid robot, any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal. The method including ceasing provision of the stimulus to the animal from the stimulator of the electronic backpack of the locomotion stimulation device in response to the corresponding one or the combination of the displacement, the velocity or the acceleration of the motion of the hybrid robot being below a pre-defined minimum displacement, a pre-defined minimum velocity or a pre-defined minimum acceleration respectively in a manner so as to allow the animal to roam freely.

According to various embodiments, there is provided an animal locomotion control system for controlling a movement of a hybrid robot using an animal as a legged platform. The animal locomotion stimulation control system including a locomotion stimulation device carriable by the animal. The locomotion stimulation device including an electronic backpack having a support structure, a positioning component coupled to the support structure, and a stimulator coupled to the support structure. The animal locomotion stimulation control system including at least a pair of electrodes for direct contact with a body part of the animal, the at least a pair of electrodes being connected to the stimulator. The animal locomotion stimulation control system including a processing unit in communication with the locomotion stimulation device. The positioning component of the electronic backpack of the locomotion stimulation device may be configured to monitor a position and an orientation of the electronic backpack of the locomotion stimulation device as a measure of a position and an orientation of the hybrid robot. The processing unit may be configured to determine an angular difference between the orientation of the electronic backpack of the locomotion stimulation device with respect to the direct path from the position of the electronic backpack to the predetermined destination. The stimulator of the electronic backpack of the locomotion stimulation device may be configured to provide a stimulus to the animal based on the angular difference determined by the processing unit. The positioning component may be further configured to monitor any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal. The stimulator of the electronic backpack of the locomotion stimulation device may be configured to cease providing the stimulus to the animal in response to the corresponding one or the combination of the displacement, the velocity or the acceleration of the motion of the hybrid robot being below a pre-defined minimum displacement, a pre-defined minimum velocity or a pre-defined minimum acceleration respectively such that the animal roam freely.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Figure 1:
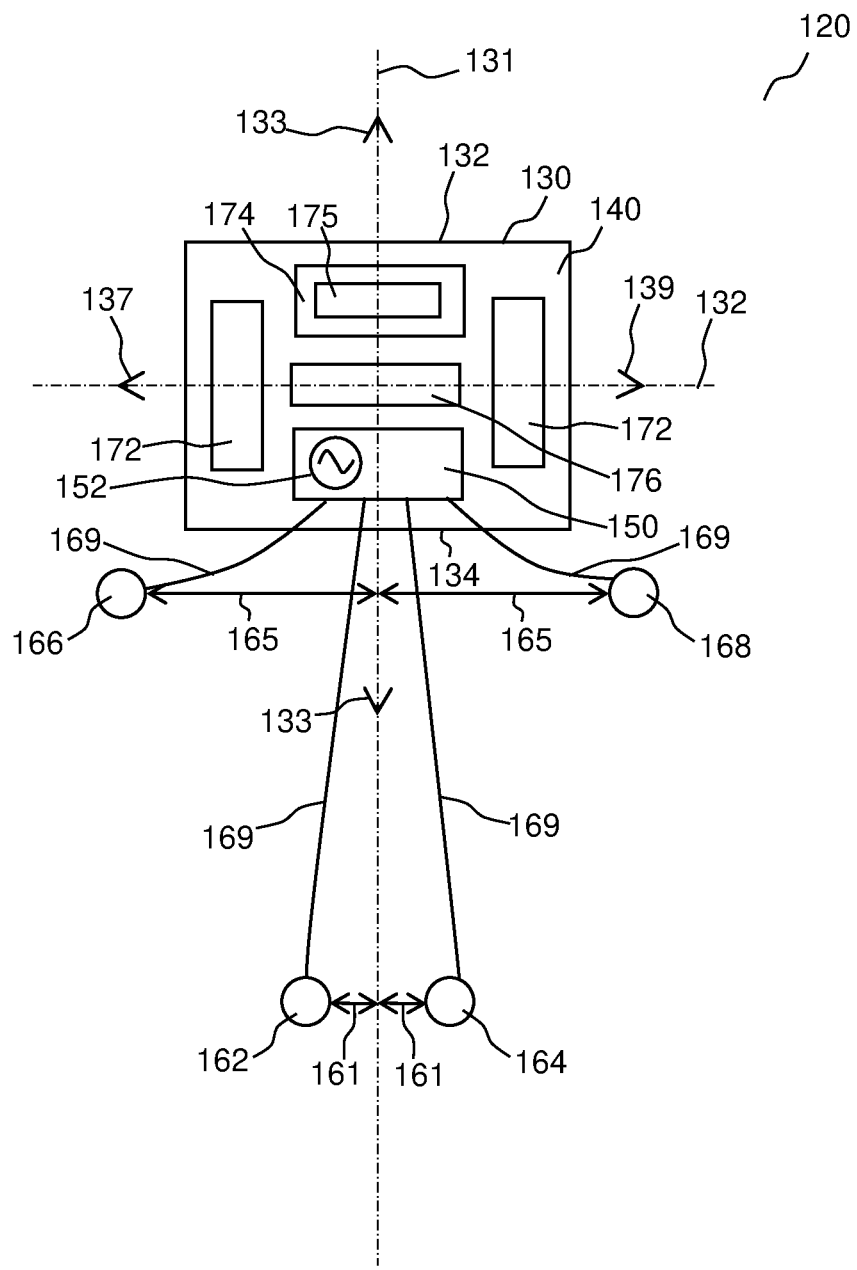
FIG. 1 shows a schematic drawing of an arthropod locomotion stimulation device according to various embodiments.

Embodiments described below in context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure. In addition, the singular terms "a", "an", and "the" include plural references unless context clearly indicates otherwise. Similarly, the word "or" is intended to include "and" unless the context clearly indicates otherwise.

In various embodiments, a "processing unit" may be understood as any kind of a logic implementing entity, which may be special purpose circuitry or a processor executing software stored in a memory, firmware, or any combination thereof. Thus, in an embodiment, a "processing unit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "processing unit" may also be a processor executing software, e.g. any kind of computer program, e.g. a computer program using a virtual machine code such as e.g. Java. Any other kind of implementation of the respective functions which will be described in more detail below may also be understood as a "processing unit" in accordance with various embodiments. In various embodiments, the "processing unit" may be part of a computing system or a controller or a microcontroller or any other system providing a processing capability. According to various embodiments, such systems may include a memory which is for example used in the processing carried out by the device or system. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magneto-resistive Random Access Memory) or a PCRAM (Phase Change Random Access Memory).

Various embodiments generally relate to a method of controlling a movement of a hybrid robot and an animal locomotion stimulation system for controlling a movement of a hybrid robot. In particular, various embodiments generally relate to a method of controlling a movement of a hybrid robot having a locomotion stimulation device carried by an animal, and an animal locomotion stimulation system for controlling a movement of a hybrid robot using an animal as a legged platform. Further, various embodiments may relate to a locomotion stimulation device, an animal locomotion control system and a method of operating the animal locomotion control system. According to various embodiments, the locomotion stimulation device may be mounted to or carried by a living animal (for example, including but not limited to mammals, reptiles, birds, amphibians, arthropods or fishes) wherein the locomotion stimulation device may be used or operated to stimulate a locomotion or movement of the animal. According to various embodiments, the animal locomotion control system may include a set of components, including the locomotion stimulation device, interconnected via a network to provide commands and/or instructions to the animal locomotion stimulation device for controlling the locomotion stimulation device to stimulate the animal's locomotion or movement so as to control or direct the locomotion or the movement of the animal. According to various embodiments, the method of operating the animal locomotion control system may include providing commands and/or instructions to the locomotion stimulation device to control the locomotion stimulation device for stimulating the animal's locomotion or movement so as to control or direct the locomotion or the movement of the animal. According to various embodiments, the locomotion or movement of the animal may be directional movement including, but not limited to, a forward movement, backward movement, a right turn, and/or a left turn. According to various embodiments, stimulation of the locomotion or movement of the animal may be for encouraging or arousing or raising a level of physiological or nervous activity in the animal associated with a tendency or inclination for the animal to move in a desired manner thereby urging or causing or induce the animal to move in the desired manner.

According to various embodiments, the device and/or the system may utilize the living animal as legged robot platforms. According to various embodiments, a combination of the locomotion stimulation device and the animal may be referred to as the hybrid robot or a biological legged machine or an animal-machine hybrid robot or a cyborg animal. According to various embodiments, the device may include a very small electronic stimulator module mounted onto the animal, for example a live insect (e.g., beetles or cockroaches), via an electronic backpack. According to various embodiments, the locomotion stimulation device may also include electrodes which may be connected to the stimulator module and may be implanted into selected areas of the animal body (e.g. an insect body) such as muscles and sensory units. According to various embodiments, the stimulator module may be controlled remotely to output electrical stimulation signals to the electrodes, which may induce the desired leg motions or walking gaits to execute the desired locomotion or movements.

According to various embodiments, manipulation of animal movements (such as insect movements) by electrically stimulating their muscles and sensory units via tiny remote controllers may require much less power than that for conventional man-made small-legged robots. This may be because the electrical stimulation of muscles or sensory units may only require a power of the order of 0.01 mW. Furthermore, complicated algorithms to traverse obstacles may be unnecessary because, when the animal (such as insect) encounters obstacles, the user may shut off the remote controller and let the animal (such as insect) traverse the obstacle independently.

According to various embodiments, the locomotion control of the living animal, such as a living insect exemplified by a Madagascar hissing cockroach which is discussed in more detail in the following, may be based on two key aspects: (1) inducement of the desired motion/walking gaits (left/right turning, forward/backward walking) in the animal (such as insect), and (2) implementation of these elicited movements to navigate the animal towards pre-determined targets.

According to various embodiments, the animal (e.g. insect such as terrestrial insect, particularly cockroach species) may possess several sensory organs helping them to collect environmental information of the surrounding. With these harvested data, the animal may be able to not only perceive the presence of obstructions then accordingly avoid or climb over, but also detect the dangerous threats then rapidly perform evasive actions. For example. two representative sensory organs in an arthropod for this procedure are antennae and cerci of the arthropod (or insect).

For example, the natural escape response of terrestrial cockroaches may be replicated using electrical stimulation. As another example, both mechanical and electrical provocations of one antenna of the Madagascar hissing cockroach may "alarm" the insect about the presence of danger at the stimulated site and subsequently "steer" it toward an opposite direction.

For example, various embodiments may intentionally direct an arthropod's locomotion (or insect locomotion, e.g. the cockroach's locomotion) via the electrical stimulation of its cerci and/or abdomen. According to various embodiments, electrical stimuli driven at the arthropod's (or insect's, e.g. cockroach's) left cercus and abdomen may induce a right turn and vice versa, whereas a stimulus applied at both cerci may accelerate the arthropod (such as insect, e.g. cockroach).

Various embodiments may include an electronic backpack that provides power to stimulate and navigate the hybrid robot. According to various embodiments, the electronic backpack may carry a payload including various equipment, electronics, and sensors, depending on the desired tasks and operations. According to various embodiments, the payload may be divided into several classes or categories or types.

First, the payload may include electronics to detect and generate location information, such as an accelerometer, an inertial measurement unit (IMU), or a global/indoor positioning system (GPS/IPS) or combination thereof. As an example, a positioning system may include beacons with known locations around a specified area and on-onboard tags to identify the location of the hybrid robots via the devices and/or system of the various embodiments as they navigate within an area (or an operating space).

Second, the payload may include communication and network electronics, such as wireless data transmission module for transmitting the locational information to a remote server or control center.

Third, the payload may include other equipment, electronics and sensors that may be required depending on the required tasks and operations, such as sensors for human sensing. Such sensors may include image and infrared sensors, acoustic sensors, pressure sensors, radar, chemical sensors, biosensors, electrochemical sensors, communication signal sensors, and any combination thereof. For other scenarios, the electronic backpack may be configured with load capacity, fastening features, lights, displays, speakers, and any combination thereof as required.

According to various embodiments, the electronic backpack may include any combinations of the three classes of equipment, electronics or sensors mentioned above, and may be configured with an integrated printed circuit board. According to various embodiments, the electronic backpack may be fitted, mounted, attached, or fastened on the animal (such as insect) to form the hybrid robot. For example, on the back or abdomen of the animal (such as insect), as exemplified in the following discussion by the Madagascar hissing cockroach. According to various embodiments, the electronic backpack may be surgically implanted into the body of the animal (such as insect).

Figure 2:
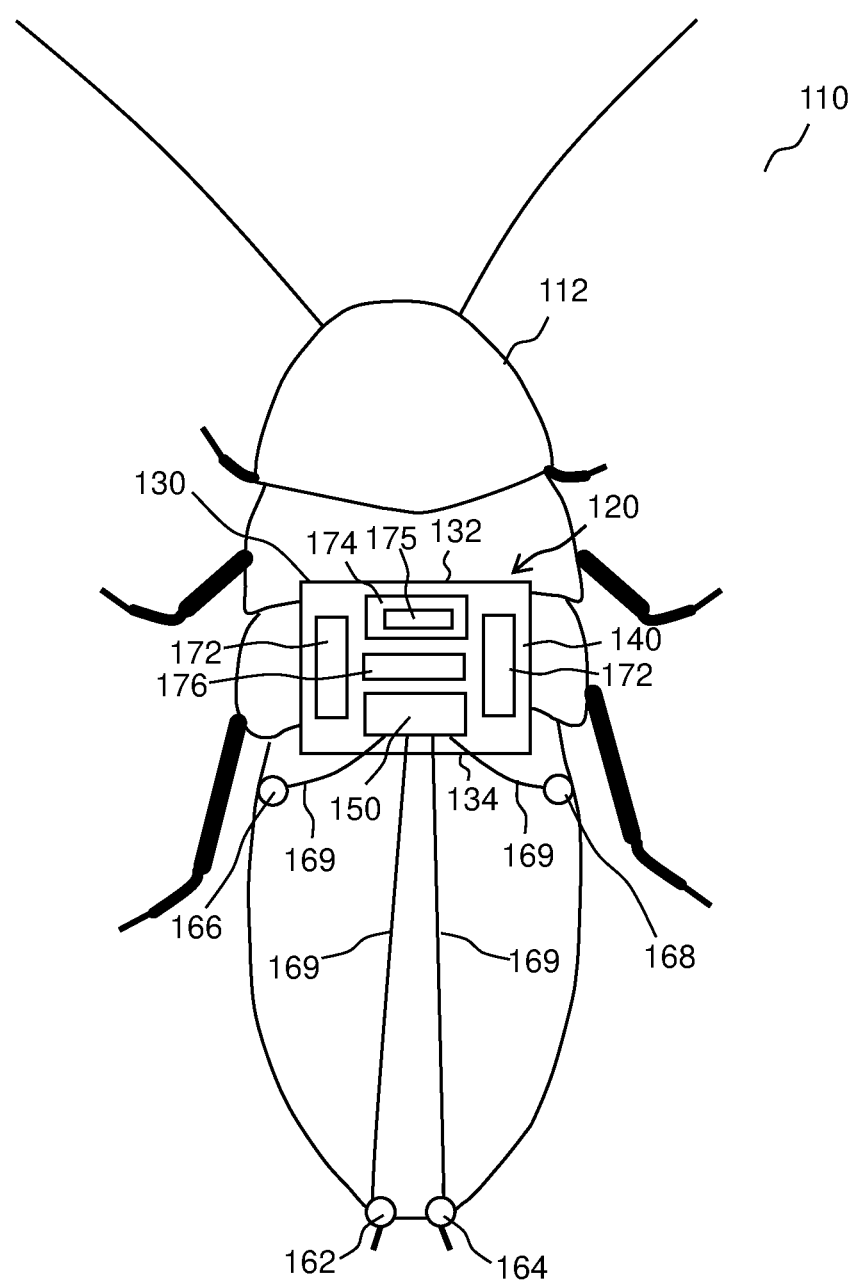
FIG. 2 shows a schematic drawing of a hybrid robot with the arthropod locomotion stimulation device of FIG. 1 on a Madagascar hissing cockroach as an example of the arthropod according to various embodiments.

FIG. 1 shows a schematic drawing of a locomotion stimulation device 120 according to various embodiments. According to various embodiments, the locomotion stimulation device 120 may be mounted to or carried by a living animal (for example as illustrated by a Madagascar hissing cockroach 112 in FIG. 2) wherein the locomotion stimulation device 120 may be used or operated to stimulate a locomotion or movement of the animal. Accordingly, the locomotion stimulation device 120 may utilize the living animal as legged robot platforms. According to various embodiments, a combination of the locomotion stimulation device 120 and the animal may be referred to as a hybrid robot or a biological legged machine or an animal-machine hybrid robot or a cyborg animal. FIG. 2 shows a schematic drawing of a hybrid robot 110 with the locomotion stimulation device 120 on a Madagascar hissing cockroach 112 as an example of the animal according to various embodiments.

According to various embodiments, the locomotion stimulation device 120 may include an electronic backpack 130. According to various embodiments, the electronic backpack 130 may be configured to be mounted, fitted, attached or fastened to the animal, or be carried by the animal, or be surgically implanted to the animal. Accordingly to various embodiments, the electronic backpack 130 may include electronic elements and/or electronic components and/or electronic circuits/circuitry integrated into a monolithic unit or package. According to various embodiments, the electronic backpack 130 may be of various shapes suitable to be mounted to or carried by the living animal.

According to various embodiments, the electronic backpack 130 may include a forward end 132 and a rear end 134. The forward end 132 of the electronic backpack 130 may be a front edge or extremity of the electronic backpack 130 that is to be aligned towards a head of the living animal when mounted to or carried by the living animal, and the rear end 134 of the electronic backpack 130 may be a back edge or extremity of the electronic backpack 130 that is opposite of the forward end 132 of the electronic backpack 130. According to various embodiments, the electronic backpack 130 may have a fore-and-aft axis 131 passing through the forward end 132 and the rear end 134 of the electronic backpack 130. Accordingly, the fore-and-aft axis 131 may be a straight line intersecting the forward end 132 of the electronic backpack 130, extending across the electronic backpack 130 from the forward end 132 to the rear end 134 and the rear end 134 of the electronic backpack 130, and intersecting the rear end 134 of the electronic backpack 130. According to various embodiments, a forward direction 133 may be defined as being extending outward from the forward end 132 of the electronic backpack 130 along the fore-and-aft axis 131. Accordingly, the forward direction 133 may be along the fore-and-aft axis 131 and pointing ahead of the forward end 132 of the electronic backpack 130. According to various embodiments, a rearward direction 135 may be defined as being extending outward from the rear end 134 of the electronic backpack 130 along the fore-and-aft axis 131. Accordingly, the rearward direction 135 may be along the fore-and-aft axis 131 and pointing in a direction opposite the forward direction 133. Hence, the forward direction 133 and the rearward direction 135 may be two opposite directions along the fore-and-aft axis 131 of the electronic backpack 130.

According to various embodiments, the electronic backpack 130 may include a transverse axis 136. The transverse axis 136 may extend across the fore-and-aft axis 131. Accordingly, the transvers axis 136 may perpendicularly intersect the fore-and-aft axis 131 in a manner resembling a cross. According to various embodiments, a left direction 137 may be defined as being extending perpendicularly away from the fore-and-aft axis 131 along the transverse axis 136 on a left side of the fore-and-aft axis 131 with respect to the forward direction 133. Accordingly, the left direction 137 may be pointing left from the fore-and-aft axis 131 with respect to the forward direction 133. According to various embodiments, a right direction 139 may be defined as being extending perpendicularly away from the fore-and-aft axis 131 along the transverse axis 136 on a right side of the fore-and-aft axis 131 with respect to the forward direction 133. Accordingly, the right direction 139 may be pointing right from the fore-and-aft axis 131 with respect to the forward direction 133. Hence, the left direction 137 and the right direction 139 may be two opposite directions along the transverse axis 136 respectively pointing to left and right with respect to the forward direction 133.

According to various embodiments, the electronic backpack 130 may include a support structure 140. According to various embodiments, the support structure 140 may may serve as a base or support or brace or bracket or arrangement for holding or keeping various components of the electronic backpack 130 together. According to various embodiments, the support structure 140 may be of any suitable shape or may be customized with various shapes, or features, or recesses, or protrusions for holding or receiving the various components of the electronic backpack 130. For example, the support structure 140 may include, but not limited to, a substrate, a panel, a board, a printed circuit board, or any other suitable structures for holding and supporting various electronic components of the electronic backpack 130. According to various embodiments, the support structure 140 may also be configured to be mounted to or carried by the animal. According to various embodiments, the support structure 140 may include mounting points or carrying points.

According to various embodiments, the electronic backpack 130 may include an electric stimulator 150 (or an electric stimulator module) coupled to the support structure 140. According to various embodiments, the electric stimulator 150 may be an electronic component configured to generate and deliver electrical pulses as stimuli. According to various embodiments, the electric stimulator 150 may receive a stimulation control signal and be operated to generate and deliver the electrical pulses based on the stimulation control signal.

According to various embodiments, when the locomotion stimulation device 120 is for an arthropod (such as the Madagascar hissing cockroach 112), the locomotion stimulation device 120 may include a first cercal-electrode insert 162 and a second cercal-electrode insert 164. According to various embodiments, each of the first cercal-electrode insert 162 and the second cercal-electrode insert 164 may be of a structure including, but not limited to, a pin structure, a pointed structure, or a probe structure, suitable to be inserted or intended for insertion into a cerci region of the arthropod.

According to various embodiments, the first cercal-electrode insert 162 and the second cercal-electrode insert 164 may be in a spaced apart side-by-side arrangement with the first cercal-electrode insert 162 being on the left side of the fore-and-aft axis 131 by a first predetermined perpendicular distance 161 and the second cercal-electrode insert 164 being on the right side of the fore-and-aft axis 131 by the same first predetermined perpendicular distance 161. Accordingly, the first cercal-electrode insert 162 and the second cercal-electrode insert 164 may be respectively disposed on the left side and the right side of the fore-and-aft axis 131 with a space therebetween in a manner such that the fore-and-aft axis 131 lies equidistant from the first cercal-electrode insert 162 and the second cercal-electrode insert 164. According to various embodiments, the first predetermined perpendicular distance 161 may correspond to a perpendicular distance of a cerci of the arthropod from a centreline of the arthropod.

According to various embodiments, the first cercal-electrode insert 162 and the second cercal-electrode insert 164 may be respectively disposed or located at predetermined positions with a predetermined rearward distance in the rearward direction 135 apart from the rear end 134 of the electronic backpack 130. According to various embodiments, the predetermined positions may correspond to the cerci region or positions of the arthropod. According to various embodiments, the first cercal-electrode insert 162 and the second cercal-electrode insert 164 may be spaced apart or separated from the rear end 134 of the electronic backpack 130 in the rearward direction 135 by the predetermined rearward distance. According to various embodiments, the predetermined rearward distance may depend on how and which part of the arthropod the electronic backpack 130 is intended to be mounted to or carried. According to various embodiments, the predetermined rearward distance may be a distance measuring from the rear end 134 of the electronic backpack 130 to the cerci region or positions of the arthropod. According to various embodiments, the first cercal-electrode insert 162 and the second cercal-electrode insert 164 may be respectively inserted into the cerci region or positions of the arthropod at the predetermined positions.

According to various embodiments, the locomotion stimulation device 120 may include a first abdominal-electrode insert 166 and a second abdominal-electrode insert 168. According to various embodiments, each of the first abdominal-electrode insert 166 and the second abdominal-electrode insert 168 may be of a structure including, but not limited to, a pin structure, a pointed structure, or a probe structure, suitable to be inserted or intended for insertion into a cerci region of the arthropod According to various embodiments, the first abdominal-electrode insert 166 and the second abdominal-electrode insert 168 may be in a spaced apart side-by-side arrangement with the first abdominal-electrode inset 166 being on the left side of the fore-and-aft axis 131 by a second predetermined perpendicular distance 165 and the second abdominal-electrode insert 168 being on the right side of the fore-and-aft axis 131 by the same second predetermined perpendicular distance 165. Accordingly, the first abdominal-electrode insert 166 and the second abdominal-electrode insert 168 may be respectively disposed on the left side and the right side of the fore-and-aft axis 131 with a space therebetween in a manner such that the fore-and-aft axis 131 lies equidistant from the first abdominal-electrode insert 166 and the second abdominal-electrode insert 168. According to various embodiments, the second predetermined perpendicular distance 165 may correspond to a perpendicular distance of a side of an abdomen region of the arthropod from the centreline of the arthropod.

According to various embodiments, the first abdominal-electrode insert 166 and the second abdominal-electrode insert 168 may be located between the forward end 132 of the electronic backpack 130 and the predetermined positions of the first cercal-electrode insert 162 and the second cercal-electrode insert 164. According to various embodiments, the first abdominal-electrode insert 166 and the second abdominal-electrode insert 168 may be located at the abdomen region of the arthropod. According to various embodiments, the first abdominal-electrode insert 166 and the second abdominal-electrode insert 168 may be located behind or rearward from the forward end 132 of the electronic backpack 130 and before or ahead of the predetermined positions of the first cercal-electrode insert 162 and the second cercal-electrode insert 164. According to various embodiments, the first abdominal-electrode insert 166 and the second abdominal-electrode insert 168 may be spaced apart or separated from the electronic backpack 130.

According to various embodiments, the electronic backpack 130 may be mounted to or carried around a thorax region of the arthropod and before the abdomen region of the arthropod. Accordingly, when the electronic backpack 130 is at the thorax region of the arthropod, the first abdominal-electrode insert 166 and the second abdominal-electrode insert 168 may be located between the rear end 134 of the electronic backpack 130 and the predetermined positions of the first cercal-electrode insert 162 and the second cercal-electrode insert 164. Hence, the electronic backpack 130, the pair of the first abdominal-electrode insert 166 and the second abdominal-electrode insert 168, and the pair of the first cercal-electrode insert 162 and the second cercal-electrode insert 164 may be arranged in sequence along a length of the arthropod from the thorax region of the arthropod to the cerci region of the arthropod. According to various embodiments, the first abdominal-electrode insert 166 and the second abdominal-electrode insert 168 may be respectively inserted into the abdomen region of the arthropod.

According to various embodiments, the second predetermined perpendicular distance 165 may be greater than the first perpendicular distance 161. According to various distance, the second predetermined perpendicular distance 165 may be at least equal to or greater than two times the first perpendicular distance 161.

According to various embodiments, each of the first cercal-electrode insert 162, the second cercal-electrode insert 164, the first abdominal-electrode insert 166 and the second abdominal-electrode insert 168 may be electrically connected to the electric stimulator 150 of the electronic backpack 130. Accordingly, the electrical pulses generated as stimuli by the electric stimulator 150 of the electronic backpack 130 may be delivered to one or a pair or a combination of the first cercal-electrode insert 162, the second cercal-electrode insert 164, the first abdominal-electrode insert 166 and the second abdominal-electrode insert 168. For example, the electrical pulses may be generated and delivered to at least two of the first cercal-electrode insert 162, the second cercal-electrode insert 164, the first abdominal-electrode insert 166 and the second abdominal-electrode insert 168. According to various embodiments, the electric stimulator 150 of the electronic backpack 130 may be configured in a manner so as to be operable to deliver electrical pulses to one or two or more of the first cercal-electrode insert 162, the second cercal-electrode insert 164, the first abdominal-electrode insert 166 and the second abdominal-electrode insert 168 based on the stimulation control signal.

According to various embodiments, each of the first cercal-electrode insert 162, the second cercal-electrode insert 164, the first abdominal-electrode insert 166 and the second abdominal-electrode insert 168 may be electrically connected to the electric stimulator 150 of the electronic backpack 130 via wired connection. According to various embodiments, a wire 169 may extend from each of the first cercal-electrode insert 162, the second cercal-electrode insert 164, the first abdominal-electrode insert 166 and the second abdominal-electrode insert 168 to the electric stimulator 150 of the electronic backpack 130.

According to various embodiments, each of the first cercal-electrode insert 162, the second cercal-electrode insert 164, the first abdominal-electrode insert 166 and the second abdominal-electrode insert 168 to the electric stimulator 150 may be integral with the respective wire 169 as a one piece structure. For example, each of the first cercal-electrode insert 162, the second cercal-electrode insert 164, the first abdominal-electrode insert 166 and the second abdominal-electrode insert 168 may respectively be a portion of the respective wire 169. Accordingly, each of the first cercal-electrode insert 162, the second cercal-electrode insert 164, the first abdominal-electrode insert 166 and the second abdominal-electrode insert 168 may respectively be a corresponding end of the respective wire 169 with an insulation or coating removed. According to various embodiments, the wire 169 may include, but not limited to, a platinum wire, or a perfluoroalkoxy (PFA) coated wire, or a PFA coated platinum wire. According to various embodiments, each of the first cercal-electrode insert 162, the second cercal-electrode insert 164, the first abdominal-electrode insert 166 and the second abdominal-electrode insert 168 may include a platinum wire. According to various embodiments, platinum may not be easily oxidized and, thus, may be durable.

According to various embodiments, the electric stimulator 150 of the electronic backpack 130 may be configured to include one or a combination of the following stimulation modes including a first electric stimulation mode, a second stimulation mode and a third stimulation mode. Accordingly, the electric stimulator 150 of the electronic backpack 130 may include one or two or all of the first electric stimulation mode, the second stimulation mode and the third stimulation mode. According to various embodiments, in the first stimulation mode, the electric stimulator 150 may be operable to provide a first electric stimulus via the first cercal-electrode insert 162 and the second cercal-electrode insert 164 for stimulating movement in the forward direction 133. According to various embodiments, in the second stimulation mode, the electric stimulator 150 may be operable to provide a second electric stimulus via the first cercal-electrode insert 162 and the first abdominal-electrode insert 164 for stimulating turning to the right direction. According to various embodiments, in the third stimulation mode, the electric stimulator 150 may be operable to provide a third electric stimulus via the second cercal-electrode insert 162 and the second abdominal-electrode insert 164 for controlling turning to the left direction. Accordingly, the electric stimulator 150 may switch between different stimulation modes such that stimulus may be provided to different pairs of the first cercal-electrode insert 162, the second cercal-electrode insert 164, the first abdominal-electrode insert 166 and the second abdominal-electrode insert 168 for stimulating movements in the forward direction 133, turning to the right direction or turning to the left direction.

According to various embodiments, the electric stimulator 150 may include a voltage source 152 to generate a voltage waveform output signal to be transmitted to one or a pair or a combination of the first cercal-electrode insert 162, the second cercal-electrode insert 164, the first abdominal-electrode insert 166 or the second abdominal-electrode insert 168. Accordingly, the first cercal-electrode insert 162, the second cercal-electrode insert 164, the first abdominal-electrode insert 166 and the second abdominal-electrode insert 168 may be connected to the voltage source 152 of the electric stimulator 150, and the electric stimulator 150 may be configured to selectively deliver or transmit the voltage waveform output signal to one or a pair or a combination of the first cercal-electrode insert 162, the second cercal-electrode insert 164, the first abdominal-electrode insert 166 and the second abdominal-electrode insert 168. According to various embodiments, the voltage waveform output signal of the voltage source 152 of the electric stimulator 150 may be an output of a periodic voltage in a waveform with a consistent peak voltage. According to various embodiments, the voltage waveform output signal may include a bipolar waveform. According to various embodiments, the electric stimulator 150 may be configured to control various parameters of the voltage waveform output signal including, but not limited to, the type of waveform, the peak voltage, and the frequency.

According to various embodiments, when the electric stimulator 150 is operating in the first electric stimulation mode, the electric stimulator 150 of the electronic backpack 130 may transmit the voltage waveform output signal serving as the first electric stimulus to the first cercal-electrode insert 162 and the second cercal-electrode insert 164. Accordingly, the electric stimulator 150 of the electronic backpack 130 may be operable to transmit or deliver the voltage waveform output signal to the first cercal-electrode insert 162 and the second cercal-electrode insert 164, and may isolate the voltage waveform output signal from being sent to the first abdominal-electrode insert 166 and the second abdominal-electrode insert 168 such that no voltage waveform output signal may be transmitted or delivered to the first abdominal-electrode insert 166 and the second abdominal-electrode insert 168.

According to various embodiments, when the electric stimulator 150 is operating in the second electric stimulation mode, the electric stimulator 150 of the electronic backpack 130 may transmit or deliver the voltage waveform output signal serving as the second electric stimulus to the first cercal-electrode insert 162 and the first abdominal-electrode insert 166. Accordingly, the electric stimulator 150 of the electronic backpack 130 may be operable to transmit or deliver the voltage waveform output signal to the first cercal-electrode insert 162 and the first abdominal-electrode insert 166, and may isolate the voltage waveform output signal from being sent to the second cercal-electrode insert 164 and the second abdominal-electrode insert 168 such that no voltage waveform output signal may be transmitted or delivered to the second cercal-electrode insert 164 and the second abdominal-electrode insert 168.

According to various embodiments, when the electric stimulator 150 is operating in the third electric stimulation mode, the electric stimulator 150 of the electronic backpack 130 may transmit or deliver the voltage waveform output signal serving as the third electric stimulus to the second cercal-electrode insert 164 and the second abdominal-electrode insert 168. Accordingly, the electric stimulator 150 of the electronic backpack 130 may be operable to transmit or deliver the voltage waveform output signal to the second cercal-electrode insert 164 and the second abdominal-electrode insert 168, and may isolate the voltage waveform output signal from being sent to the first cercal-electrode insert 162 and the first abdominal-electrode insert 166 such that no voltage waveform output signal may be transmitted or delivered to the first cercal-electrode insert 162 and the first abdominal-electrode insert 166.

As an example, according to various embodiments, the voltage waveform output signal generated by the electric stimulator 150 of the electronic backpack 130 may include, but not limited to, a bipolar square wave having a peak to peak voltage (Vpp) in a range of 4 volts to 20 volts and a frequency in a range of 10 Hz to 50 Hz.

According to various embodiments, the electronic backpack 130 may include one or more task-specific components 172 coupled to the support structure 140. According to various embodiments, the task-specific components 172 may include sensor components, emitter components, transmitter components, receiver components, or any other components for performing the tasks or operations required by the hybrid robot (for example see 110 of FIG. 2). According to various embodiments, the task-specific components 172 may include, but not limited to, an image sensor, an infrared sensor, an acoustic sensor, a pressure sensor, a radar, a chemical sensor, a biosensor, an electrochemical sensor, a communication signal sensor, a fastening feature, a light, a display, a speaker, or any combination thereof as required.

According to various embodiments, the electronic backpack 130 may include a communication module 174 coupled to the support structure 140. According to various embodiments, the communication module 174 may be connected with an external processing unit (for example see 102 in FIG. 3) via a wired or wireless communication. According to various embodiments, the communication module 174 may include a communication port 175 for the wired or wireless communication. According to various embodiments, the communication port 175 of the communication module 174 may include, but not limited to, a wireless fidelity (WiFi) port, a wireless local area network (WLAN) port, an infrared port, or a Bluetooth port for wireless communication. According to various embodiments, the communication port 175 of the communication module 174 may include, but not limited to, a pin/pins port, a universal serial bus (USB) port, or a registered jack (RJ) port for wired communication. According to various embodiments, the communication module 174 of the electronic backpack 130 may establish communication with the external processing unit 102 for programming or configuring the electrical stimulator 150 of the electronic backpack 130 and/or controlling the electrical stimulator 150 of the electronic backpack 130 and/or real-time control of the electrical stimulator 150 of the electronic backpack 130.

According to various embodiments, the electronic backpack 130 may include a positioning component 176 coupled to the support structure 140. According to various embodiments, the positioning component 176 may determine a (current) position and/or orientation and/or displacement and/or velocity and/or acceleration of the electronic backpack 130 of the locomotion control device 120 as a (current) position and/or orientation and/or displacement and/or velocity and/or acceleration of the hybrid robot 110 with respect to an operating space of the locomotion control device 120. According to various embodiments, the position may be a location or a point in the operating space of the locomotion control device 120. According to various embodiments, the orientation may be a facing or a heading or a direction or a bearing of the forward end 132 of the electronic backpack 130. According to various embodiments, the displacement may be a linear or an angular distance moved by the electronic backpack 130. According to various embodiments, the velocity may be a speed or a rate of change of position of the electronic backpack 130. According to various embodiments, the acceleration may be a rate of change of velocity or speed. According to various embodiments, the positioning component 176 may be a standalone component for determining the position and/or orientation and/or displacement and/or velocity and/or acceleration of the electronic backpack 130. For example, the positioning component 176 may include, but not limited to, an inertial measurement unit (IMU). The IMU may include an accelerometer and/or a gyroscope for determining the position and/or orientation and/or displacement and/or velocity and/or acceleration of the electronic backpack 130. According to various embodiments, the positioning component 176 may include a tracking or navigation or receiver unit which is part of a positioning system and which may interact with other components (e.g. positioning reference units 178 or beacons) of the positioning system to determine the position and/or orientation and/or displacement and/or velocity and/or acceleration of the electronic backpack 130. For example, the positioning component 176 may include, but not limited to, a tracking or navigation or receiver unit of a global navigational satellite system (GNSS), a global positioning system (GPS), a local positioning system, or an indoor positioning system.

According to various embodiments, FIG. 2 shows the locomotion stimulation device 120 of FIG. 1 being mounted to or carried by a Madagascar hissing cockroach 112 as an example of the animal. Accordingly, FIG. 2 shows the hybrid robot 110 being a combination of the locomotion stimulation device 120 of FIG. 1 and the Madagascar hissing cockroach 112 (being an example of the animal). According to various embodiments, as shown, the electronic backpack 130 of the locomotion stimulation device 120 may be mounted to or carried on a back of the thorax region of the Madagascar hissing cockroach 112. According to various embodiments, beeswax may be used to mount the electronic backpack 130 of the locomotion stimulation device 120 to the Madagascar hissing cockroach 112. According to various embodiments, the electronic backpack 130 of the locomotion stimulation device 120 may be oriented such that the fore-and-aft axis 131 is aligned to a length of the Madagascar hissing cockroach 112. Accordingly, the forward direction 133 extending from the forward end 132 of the electronic backpack 130 may correspond to a forward movement of the Madagascar hissing cockroach 112 (or in a direction which the head of the Madagascar hissing cockroach 112 is facing), the rearward direction 135 extending from the rear end 134 of the electronic backpack 130 may correspond to a backward or reverse movement of the Madagascar hissing cockroach 112, the left direction 137 of the electronic backpack 130 may correspond to a left of the Madagascar hissing cockroach 112 and the right direction 139 may correspond to a right of the Madagascar hissing cockroach 112.

According to various embodiments, as shown, the first cercal-electrode insert 162 and the second cercal-electrode insert 164 of the locomotion stimulation device 120 may be inserted into the cerci region of the Madagascar hissing cockroach 112. According to various embodiments, the predetermined positions of the first cercal-electrode insert 162 and the second cercal-electrode insert 164 of the locomotion stimulation device 120 may correspond to positions of the two cerci of the Madagascar hissing cockroach 112. According to various embodiments, the first cercal-electrode insert 162 and the second cercal-electrode insert 164 of the locomotion stimulation device 120 may be spaced across a length of the abdomen of the Madagascar hissing cockroach 112 from the rear end 134 of the electronic backpack 130.

According to various embodiments, as shown, the first cercal-electrode insert 162 and the second cercal-electrode insert 164 of the locomotion stimulation device 120 may be inserted into two opposite sides of the abdomen region of the Madagascar hissing cockroach 112. According to various embodiments, the first cercal-electrode insert 162 and the second cercal-electrode insert 164 of the locomotion stimulation device 120 may be located between the rear end 134 of the electronic backpack 130 and the pair of the first cercal-electrode insert 162 and the second cercal-electrode insert 164 of the locomotion stimulation device 120 along the length of the Madagascar hissing cockroach 112. According to various embodiments, the first cercal-electrode insert 162 and the second cercal-electrode insert 164 of the locomotion stimulation device 120 may be inserted into two opposite sides of the abdomen region of the Madagascar hissing cockroach 112 after the rear end 134 of the electronic backpack 130 of the locomotion stimulation device 120.

Figure 3:
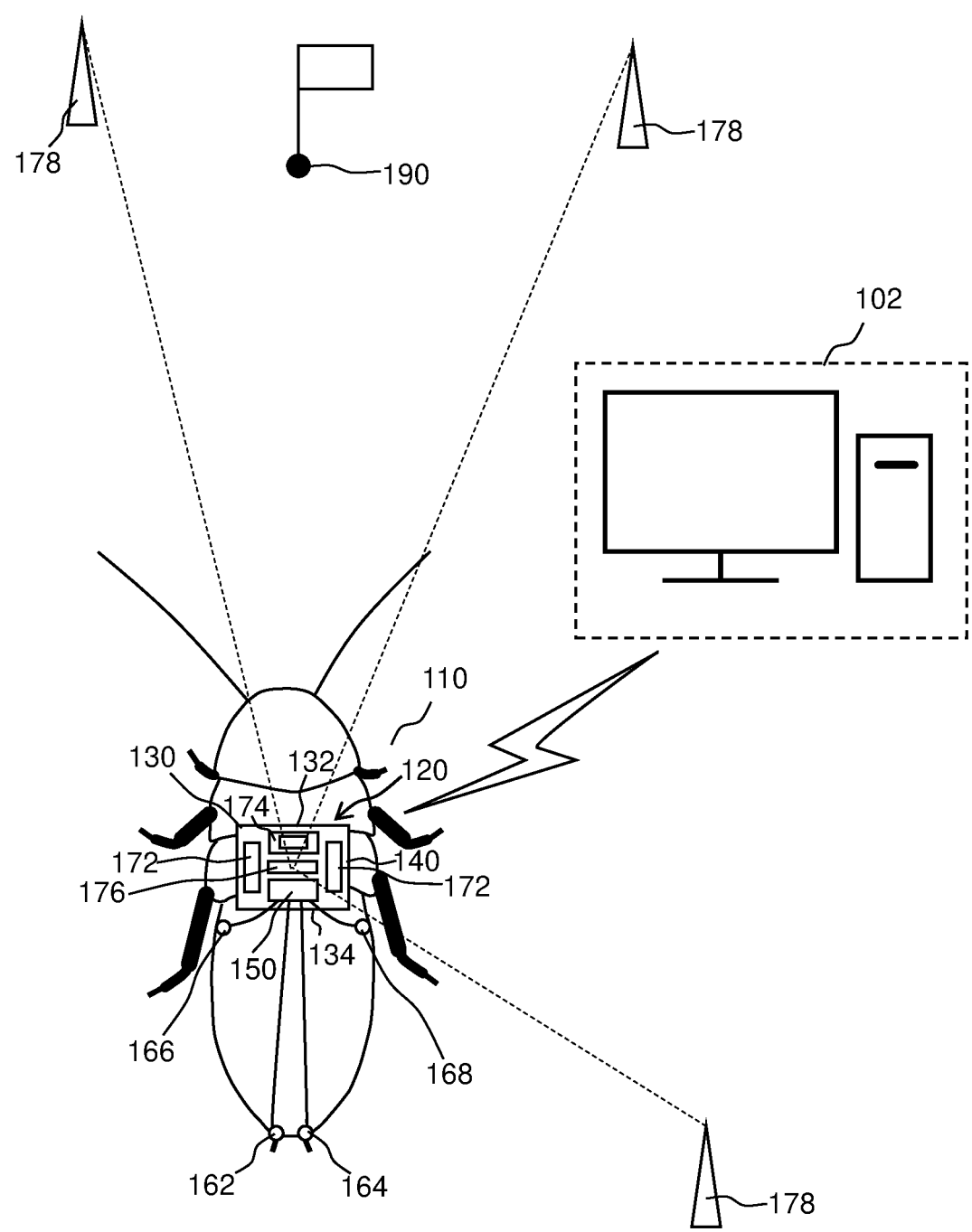
FIG. 3 shows an arthropod locomotion control system according to various embodiments.

FIG. 3 shows an animal locomotion control system 100 according to various embodiments. According to various embodiments, the animal locomotion control system 100 may include the locomotion stimulation device 120 of FIG. 1 and the external processing unit 102. According to various embodiments, the external processing unit 102 may be connected to the locomotion stimulation device 120 via the wired or wireless communication. In the drawings, the Madagascar hissing cockroach 112 is shown as an example of the animal in FIG. 3.

According to various embodiments, the positioning component 176 of the electronic backpack 130 of the locomotion stimulation device 120 may be configured to determine the (current) position and/or orientation and/or displacement and/or velocity and/or acceleration of the electronic backpack 130 as the (current) position and/or orientation and/or displacement and/or velocity and/or acceleration of the hybrid robot 110 with respect to the operating space of the locomotion control device 120. Accordingly, the positioning component 176 of the electronic backpack 130 may actively determine the position and/or orientation and/or displacement and/or velocity and/or acceleration of the hybrid robot 110 via determining the position and/or orientation and/or displacement and/or velocity and/or acceleration of the electronic backpack 130 within the operating space of the locomotion control device 120.

According to various embodiments, the communication module 174 of the electronic backpack 130 of the locomotion control device 120 may be configured to send the position and/or orientation and/or displacement and/or velocity and/or acceleration of the electronic backpack 130 to the external processing unit 102. Accordingly, upon determining the position and/or orientation and/or displacement and/or velocity and/or acceleration of the electronic backpack 130 within the operating space of the locomotion control device 120, the electronic backpack 130 may send the position and/or orientation and/or displacement and/or velocity and/or acceleration via the communication module 174 of the electronic backpack 130 to the external processing unit 102.

According to various embodiments, the external processing unit 102 may be configured to determine the stimulation control signal to be sent to the electronic backpack 130 of the arthropod locomotion control device 120 based on comparing the position and orientation (or angular position) of the electronic backpack 130 and a predetermined destination 190 of the electronic backpack 130 as a destination of the hybrid robot 110 within the operating space of the locomotion control device 120. Accordingly, the external processing unit 102 may utilize information relating to the position and orientation of the electronic backpack 130 and the predetermined destination 190 of the electronic backpack 130 so as to determine whether to send the stimulation control signal and what stimulation control signal is to be sent. Hence, the external processing unit 102 may process the position and the orientation of the electronic backpack 130 and the predetermined destination 190 of the electronic backpack 130 for determining the stimulation control signal to be sent to the electronic backpack 130. According to various embodiments, the external processing unit 102 may receive the position and the orientation of the electronic backpack 130 as an input from the electronic backpack 130 and generate a corresponding response via the stimulation control signal as an output from the external processing unit 102 to the electronic backpack 130. According to various embodiments, the stimulation control signal may include a command or instructions to operate the electric stimulator 150 of the electronic backpack 130 in the first electric stimulation mode, the second electric stimulation mode, or the third electric stimulation mode.

According to various embodiments, the communication module 174 of the electronic backpack 130 of the locomotion control device 120 may be configured to receive the stimulation control signal from the external processing unit 102. Accordingly, upon receiving the stimulation control signal from the external processing unit 102, the communication module 174 of the electronic backpack 130 may direct the stimulation control signal to the electric stimulator 150 of the electronic backpack 130.

According to various embodiments, the electric stimulator 150 of the electronic backpack 130 may be operated based on the stimulation control signal from the external processing unit 102. Accordingly, depending on the common or instructions in the stimulation control signal, the electric stimulator 150 of the electronic backpack 130 may generate a corresponding stimulus.

According to various embodiments, the external processing unit 102 may be configured to determine whether to cease the stimulus provided by the electric stimulator 150 based on comparing the displacement and/or the velocity and/or the acceleration of the electronic backpack 130 in response to the stimulus against a pre-defined minimum displacement and/or a pre-defined minimum velocity and/or a pre-defined minimum acceleration respectively. Accordingly, the external processing unit 102 may utilize information relating to the displacement and/or the velocity and/or the acceleration of the electronic backpack 130 so as to determine whether to send a cease-stimulation control signal. According to various embodiments, the external processing unit 102 may receive the displacement and/or the velocity and/or the acceleration of the electronic backpack 130 as an input from the electronic backpack 130 and generate a corresponding response via the cease-stimulation control signal as an output from the external processing unit 102 to the electronic backpack 130. When the cease-stimulation control signal is sent, the electric stimulator 150 of the electronic backpack 130 may not send any stimulus. Hence, the hybrid robot 110 may roam freely or the animal (e.g. the Madagascar hissing cockroach 112) may move freely without any stimulation from the electric stimulator 150 of the electronic backpack 130.

According to various embodiments, the animal locomotion control system 100 may include one or more positioning reference units 178 from which the positioning component 176 of the locomotion control device 120 may determine the position and/or orientation and/or displacement and/or velocity and/or acceleration of the electronic backpack 130 with respect to the operating space of the locomotion control device 120 via position fixing methods. Accordingly, the positioning component 176 of the locomotion control device 120 may interact with the one or more positioning reference units 178 for determining the position of the electronic backpack 130. According to various embodiments, the one or more positioning reference units 178 may include positioning markers, positioning beacons, positioning transmitters, positioning satellites, etc. Accordingly, the positioning component 176 of the locomotion control device 120 may receive or obtain reference positions information and/or bearing information from the reference positions and/or measurements with respect to the reference positions for determining position of the electronic backpack 130 via electronic fixing methods. According to various embodiments, the animal locomotion control system 100 may include three or more positioning reference units 178. According to various embodiments, the positioning component 176 of the locomotion control device 120 and the one or more positioning reference units 178 may together form a positioning system. According to various embodiments, the positioning system may include, but not limited to, a global navigational satellite system (GNSS), a global positioning system (GPS), a local positioning system, or an indoor positioning system.

Figure 4:
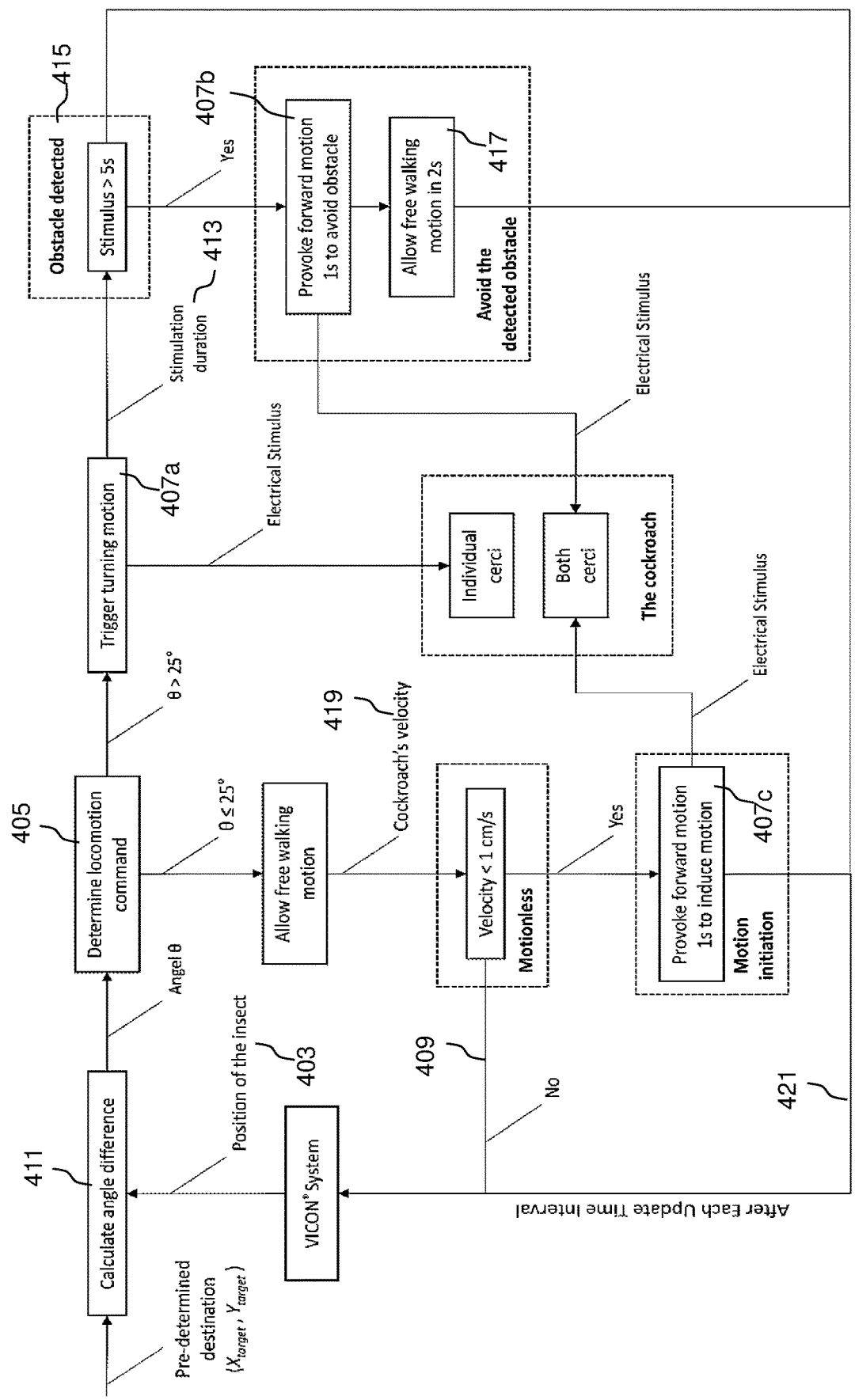
FIG. 4 shows a flow diagram of a method of operating the arthropod locomotion control system of FIG. 3 according to various embodiments.

FIG. 4 shows a flow diagram of a method 101 of operating the arthropod locomotion control system 100 of FIG. 3 according to various embodiments. According to various embodiments, the method 101 may (e.g. see 403) include determining, via the positioning component 176 of the electronic backpack 130 of the arthropod locomotion control device 120, the (current) position and orientation of the electronic backpack 130 as the (current) position and orientation of the hybrid robot 110 with respect to the operating space of the locomotion control device 120. Accordingly, the positioning component 176 of the electronic backpack 130 may perform the determination of the position and orientation of the electronic backpack 130 with respect to the operating space of the arthropod locomotion control device 120.

According to various embodiments, the method 101 may (e.g. see 405) include determining, via the external processing unit 102, the stimulation control signal to be sent to the electronic backpack 130 of the arthropod locomotion control device 120 based on comparing the position and orientation of the electronic backpack 130 and the predetermined destination 190 of the electronic backpack 130 within the operating space of the locomotion control device 120. According to various embodiments, the predetermined destination 190 of the electronic backpack 130 may be the predetermined destination of the hybrid robot 110. According to various embodiments, the external processing unit 102 may perform the determination of the stimulation control signal from comparing the position and orientation of the electronic backpack 130 and the predetermined destination 190 of the electronic backpack 130 within the operating space of the locomotion control device 120.

According to various embodiments, the method 101 may (e.g. see 407a, 407b, 407c) include operating the electric stimulator 150 of the electronic backpack 130 of the locomotion control device 120 based on the stimulation control signal from the external processing unit 102. Accordingly, the electric stimulator 150 of the electronic backpack 130 may operate to transmit or deliver stimulus to one or a pair or a combination of electrodes (for example a pair or a combination of the first cercal-electrode insert 162, the second cercal-electrode insert 164, the first abdominal-electrode insert 166 or the second abdominal-electrode insert 168) according to the stimulation control signal from the external processing unit 102. For example, the electric stimulator 150 may operate to provide the first electric stimulus via the first cercal-electrode insert 162 and the second cercal-electrode insert 164 for stimulating movement in the forward direction 133, or the second electric stimulus via the first cercal-electrode insert 162 and the first abdominal-electrode insert 164 for stimulating turning to the right direction, or the third electric stimulus via the second cercal-electrode insert 162 and the second abdominal-electrode insert 164 for controlling turning to the left direction according to the stimulation control signal from the external processing unit 102.

According to various embodiments, the method 101 may (e.g. see 409) include that determining the position and orientation of the electronic backpack 130 with respect to the operating space of the arthropod locomotion control device 120 may be resumed or repeated after a predetermined fixed interval of no stimulus being provided by the electric stimulator 150. Accordingly, the positioning component 176 of the electronic backpack 130 may regularly perform the determination of the position and orientation of the electronic backpack 130 with respect to the operating space of the arthropod locomotion control device 120 at the predetermined fixed interval when no stimulus is being provided by the electric stimulator 150.

According to various embodiments, the method 101 may include that, when the external processing unit 102 is determining the stimulation control signal to be sent, the external processing unit 102 may perform determination of the angular difference between the orientation of the electronic backpack 130 and the direct path to the predetermined destination 190. The orientation of the electronic backpack 130 may be obtained from the positioning component 176 of the electronic backpack 130. The direct path may be based on joining the position of the electronic backpack 130 and the predetermined destination 190 using a straight line. Hence, the angular difference may be an angle formed between the orientation of the electronic backpack 130 and the straight line representing the direct path to the predetermined destination 190. Thus, the angular difference may serve as a measure of whether the hybrid robot 110 is facing the predetermined destination 190.

According to various embodiments, the method 101 may include that determining the stimulation control signal to be sent may include (see 407a) sending a steering stimulation control signal to steer the locomotion control device 120 such that the electric stimulator 150 may provide a stimulus to the animal when the angular difference is greater than a pre-defined threshold. Accordingly, the external processing unit 102 may send the steering stimulation control signal upon determining that the angular difference is greater than the pre-defined threshold. Hence, the external processing unit 102 may determine whether the angular difference is greater than the pre-defined threshold, and may send the steering stimulation control signal when the angular difference is greater than the pre-defined threshold. Thus, the angular difference may serve as an indication that the hybrid robot 110 is not facing the predetermined destination 190. For example, an absolute magnitude of the angular difference may be used to determine whether the angular difference is greater than the pre-defined threshold. Further, a sign (e.g. positive or negative) of the angular difference may be used to determine whether to send a steering stimulation control signal for turning left or a steering stimulation control signal for turning right. According to various embodiments, the pre-defined threshold may be set such that, when the angular difference is greater than the pre-defined threshold, the hybrid robot 110 may be considered not to be facing the predetermined destination 190 and the chances of reaching the predetermined destination 190 by only forward movement may be low. On the other hand, when the angular difference is equal or lesser than the pre-defined threshold, the hybrid robot 110 may be considered to be facing the predetermined destination 190 and the chances of reaching the predetermined destination 190 by only forward movement may be high. According to various embodiments, the pre-defined threshold may be dependent on the type of animal being used as the legged platform of the hybrid robot 110. According to various embodiments, when the animal is the Madagascar hissing cockroach 112, the pre-defined threshold may be between 20° to 50°. For example, the predefined threshold may be 20°, or 25°, or 30°, or 35°, or 40°, or 45°, or 50°. According to various embodiments, the steering stimulation control signal may include stimulation control signals for turning left or turning right depending on which side of the direct path the angular difference is formed. Accordingly, based on the steering stimulation control signal from the external processing unit 102, the electronic backpack 130 of the arthropod locomotion control device 120 may operate the electric stimulator 150 to provide the second electric stimulus via the first cercal-electrode insert 162 and the first abdominal-electrode insert 164 for stimulating turning to the right direction, or the third electric stimulus via the second cercal-electrode insert 162 and the second abdominal-electrode insert 164 for controlling turning to the left direction so as to steer the hybrid robot 110 back towards the predetermined destination 190.

According to various embodiments, the method 101 may include that determining the stimulation control signal to be sent may include sending the steering stimulation control signal to steer the arthropod locomotion control device for a predetermined period of time (see 413); and monitoring, after the predetermined period of time, any one or a combination of a displacement, a velocity or an acceleration of the electronic backpack 130 via the positioning component 176 of the electronic backpack 130 as a measure of a corresponding one or a combination of a displacement, a velocity or an acceleration of a motion of the hybrid robot 110 in response to the stimulus provided to the animal. The one or the combination of the displacement, the velocity or the acceleration may include one or a combination of an angular displacement, an angular velocity, or an angular acceleration. Further, the method 101 may include ceasing provision of the stimulus to the animal when the one or the combination of the displacement, the velocity or the acceleration of the electronic backpack 130 is less than a pre-defined minimum displacement, a pre-defined minimum velocity or a pre-defined minimum acceleration respectively.

The predefined minimum displacement, the pre-defined minimum velocity or the pre-defined minimum acceleration may be a predefined minimum angular displacement, a pre-defined minimum angular velocity or a pre-defined minimum angular acceleration. The predefined minimum displacement, the pre-defined minimum velocity or the pre-defined minimum acceleration may be dependent on the type of animal. Accordingly, different value or magnitude of the predefined minimum displacement, the pre-defined minimum velocity or the pre-defined minimum acceleration may be set so as to match a sensitivity of the predefined minimum displacement, the pre-defined minimum velocity or the pre-defined minimum acceleration with respect to the motion of different type of animal. Further, the predefined minimum displacement, the pre-defined minimum velocity or the pre-defined minimum acceleration may be set so as to serve as an indication that the animal has encountered an obstacle. According to various embodiments, the external processing unit 102 may send the steering stimulation control signal for the predetermined period of time. According to various embodiments, the predetermined period of time may be between 3 seconds to 8 seconds. For example, the predetermined period of time may be 3 seconds, or 4 seconds, or 5 seconds, or 6 seconds, or 7 seconds, or 8 seconds. According to various embodiments, after sending the steering stimulation control signal, the one or the combination of the displacement, the velocity or the acceleration of the electronic backpack 130 may be monitored via the positioning component 176. According to various embodiments, if the one or the combination of the displacement, the velocity or the acceleration is less than the pre-defined minimum displacement, the pre-defined minimum velocity or the pre-defined minimum acceleration respectively despite the steering stimulation control signal being sent for the predetermined period of time, the path of the hybrid robot 110 may be considered to be obstructed (see 415). Hence, the external processing unit 102 may send a cease-stimulation control signal to cease providing the stimulus to the animal.

According to various embodiments, in response to the one or the combination of the displacement, the velocity or the acceleration of the electronic backpack 130 being below the pre-defined minimum displacement, the pre-defined minimum velocity or the pre-defined minimum acceleration respectively, the method 101 may further include providing an acceleration stimulus, via the electric stimulator 150 of the electronic backpack of the locomotion stimulation device, to induce acceleration of the animal after ceasing provision of the stimulus to the animal; and ceasing provision of the acceleration stimulus to the animal from the stimulator of the electronic backpack of the locomotion stimulation device after a first period of time of providing the acceleration stimulus. Accordingly, the processing unit 102 may send an acceleration stimulation control signal to induce acceleration of the animal or to provide an impetus to move such that the animal may be induced to accelerate forward so as to move to overcome the obstacle on its own. According to various embodiments, the acceleration stimulation control signal (see 407b) may be provided for the first period of time whereby the processing unit 102 may send a cease-acceleration stimulation control signal to the electronic backpack 130 after the first period of time in order for the electric stimulator 150 to cease providing the acceleration stimulus to the animal. Accordingly, the animal may move freely on its own to overcome the obstacle after the acceleration stimulus, which have been provided to induce an acceleration motion or an impetus to move for the first period of time, has ceased. According to various embodiments, the first period of time may be 1 second, or 2 seconds, or 3 seconds, or 4 seconds, or 5 seconds. According to various embodiments, the method 101 may include resuming the monitoring of the position and orientation of the electronic backpack 130 of the locomotion stimulation device 120 after a second period of time of ceasing provision of the acceleration stimulus to the animal (see 417). According to various embodiments, the second period of time may be 1 second, or 2 seconds, or 3 seconds, or 4 seconds, or 5 seconds.

According to various embodiments, the method 101 may include that determining the stimulation control signal to be sent may include (see 419) that, when the angular difference is equal or less than the pre-defined threshold, the processing unit 102 may not provide any stimulation control signal to the electronic backpack 130 such that no stimulus is provided to the animal. Accordingly, the path of the hybrid robot 110 when the animal is moving freely may be considered to be heading towards the predetermined destination 190, thus, no further stimulation may be required to steer or induce the animal to move towards the predetermined destination 190. Hence, the angular difference being equal or less than the pre-defined threshold may serve as an indication that the hybrid robot 110 is facing or heading towards the predetermined destination 190. According to various embodiments, the method 101 may include monitoring the one or the combination of the displacement, the velocity or the acceleration of the electronic backpack 130 via the positioning component 176 of the electronic backpack 130 as a measure of a corresponding one or a combination of a displacement, a velocity or an acceleration of a motion of the hybrid robot 110 when no stimulus is provided to the animal. The one or the combination of the displacement, the velocity or the acceleration may include one or a combination of a linear displacement, a linear velocity, or a linear acceleration. Further, the method 101 may include (see 407c) sending an acceleration stimulation control signal for providing an acceleration stimulus to induce the animal for forward motion when the one or the combination of the displacement, the velocity or the acceleration of the electronic backpack 130 is less than a pre-defined minimum displacement, a pre-defined minimum velocity or a pre-defined minimum acceleration respectively. When the one or the combination of the displacement, the velocity or the acceleration of the electronic backpack 130 is less than a pre-defined minimum displacement, a pre-defined minimum velocity or a pre-defined minimum acceleration respectively, the animal may be considered to either have slowed down to rest or may have encountered an obstacle. Accordingly, when the angular difference is determined to be equal or less than the pre-defined threshold by the external processing unit 102, the external processing unit 102 may determine whether the one or the combination of the displacement, the velocity or the acceleration of the electronic backpack 130 is less than the pre-defined minimum displacement, the pre-defined minimum velocity or the pre-defined minimum acceleration respectively. When the one or the combination of the displacement, the velocity or the acceleration of the electronic backpack 130 is less than the pre-defined minimum displacement, the pre-defined minimum velocity or the pre-defined minimum acceleration respectively, the external processing unit 102 may send the forward stimulation control signal to induce a forward acceleration of the hybrid robot 110 so as to increase the velocity of the hybrid robot 110. For example, when the animal is the Madagascar hissing cockroach 112, the pre-defined minimum velocity may be between 0.5 cm/s to 1.5 cm/s. For example, the pre-defined minimum velocity may be 0.5 cm/s, or 1 cm/s, or 1.5 cm/s.

According to various embodiments, the method 101 may include ceasing provision of the acceleration stimulus to the animal from the stimulator of the electronic backpack 130 of the locomotion stimulation device 120 after a first period of time of providing the acceleration stimulus. Accordingly, the forward stimulation control signal (see 407c) may be provided for the first period of time whereby the processing unit 102 may send a cease-forward stimulation control signal to the electronic backpack 130 after the first period of time in order for the electric stimulator 150 to cease providing the acceleration stimulus to the animal. Accordingly, the animal may be induced to continue moving forward towards the predetermined destination on its own or to move freely on its own to overcome the obstacle after the acceleration stimulus, which have been provided to induce to forward motion for the first period of time, has ceased. According to various embodiments, the first period of time may be 1 second, or 2 seconds, or 3 seconds, or 4 seconds, or 5 seconds. According to various embodiments, the method 101 may include resuming the monitoring of the position and orientation of the electronic backpack 130 of the locomotion stimulation device 120 after a second period of time of ceasing provision of the acceleration stimulus to the animal (see 421). According to various embodiments, the second period of time may be 1 second, or 2 seconds, or 3 seconds, or 4 seconds, or 5 seconds.

According to various other embodiments (not shown), the method 101 may include that determining the stimulation control signal to be sent may include (see 419) that, when the angular difference is equal or less than the pre-defined threshold, the processing unit 102 may provide a forward stimulus for stimulating movement in a forward direction; and, after a predetermined period of time, any one or a combination of a displacement, a velocity or an acceleration of the electronic backpack 130 may be monitored via the positioning component 176 of the electronic backpack 130 as a measure of a corresponding one or a combination of a displacement, a velocity or an acceleration of a motion of the hybrid robot 110 in response to the stimulus provided to the animal. Accordingly, the hybrid robot 110 may be assumed to be heading towards the predetermined destination 190 since the angular difference is equal or less than the pre-defined threshold. Hence, the processing unit 102 may send a forward stimulation control signal to the electronic backpack 130 of the locomotion stimulation device 120 such that the electric stimulator 150 may generate the forward stimulus to continue guiding the animal to move towards the predetermined destination 190. Subsequently, the one or the combination of the displacement, the velocity or the acceleration of the motion of the hybrid robot 101 may be monitored. The one or the combination of the displacement, the velocity or the acceleration may include one or a combination of a liner displacement, a linear velocity, or a linear acceleration. Further, the method 101 may include ceasing provision of the stimulus to the animal when the one or the combination of the displacement, the velocity or the acceleration of the electronic backpack 130 is less than a pre-defined minimum displacement, a pre-defined minimum velocity or a pre-defined minimum acceleration respectively. The predefined minimum displacement, the pre-defined minimum velocity or the pre-defined minimum acceleration may be a predefined minimum linear displacement, a pre-defined minimum linear velocity or a pre-defined minimum linear acceleration. The predefined minimum displacement, the pre-defined minimum velocity or the pre-defined minimum acceleration may be dependent on the type of animal. Accordingly, different value or magnitude of the predefined minimum displacement, the pre-defined minimum velocity or the pre-defined minimum acceleration may be set so as to match a sensitivity of the predefined minimum displacement, the pre-defined minimum velocity or the pre-defined minimum acceleration with respect to the motion of different type of animal. Further, the predefined minimum displacement, the pre-defined minimum velocity or the pre-defined minimum acceleration may be set so as to serve as an indication that the animal has encountered an obstacle. According to various embodiments, the predetermined period of time may be between 3 seconds to 8 seconds. For example, the predetermined period of time may be 3 seconds, or 4 seconds, or 5 seconds, or 6 seconds, or 7 seconds, or 8 seconds. According to various embodiments, if the one or the combination of the displacement, the velocity or the acceleration is less than the pre-defined minimum displacement, the pre-defined minimum velocity or the pre-defined minimum acceleration respectively despite the forward stimulation control signal being sent for the predetermined period of time, the path of the hybrid robot 110 may be considered to be obstructed. Hence, the external processing unit 102 may send a cease-stimulation control signal to cease providing the stimulus to the animal such that the animal may roam freely to overcome the obstacle.

The following descriptions describe the locomotion control device 120, the system 100 and the method 101 of the various embodiments as demonstrated by a prototype implementing the animal locomotion control using the Madagascar hissing cockroach 112 as an example.

According to various embodiments, for example in the prototype, an implantation may include four PFA-Coated Platinum wires (76.2 μm bare-139.7 μm coated diameter—A-M Systems) being prepared as stimulating electrodes (as examples for the first cercal-electrode insert 162, the second cercal-electrode insert 164, the first abdominal-electrode insert 166 and the second abdominal-electrode insert 168). One end of these four wires may be connected to an electronic stimulation source (i.e., electronic stimulator module on a wireless backpack or the electric stimulator 150 on the electronic backpack 130). The insulation of the other ends may be removed using twister at the length of 1 cm for two electrodes (serving as cercal electrodes; or the first cercal-electrode insert 162 and the second cercal-electrode insert 164) and 0.5 cm for the other two (serving as abdominal electrodes; or the first abdominal-electrode insert 166 and the second abdominal-electrode insert 168). The Madagascar hissing cockroach 112 may then be anesthetized using carbon dioxide (or $CO_2$) gas for immobilization. Afterward, the tips of two cerci may be trimmed off to create two small openings, and two cercal stimulating electrodes (or the first cercal-electrode insert 162 and the second cercal-electrode insert 164) may then be inserted into these holes at a depth of 1 cm. The insertion may be fixed in position using beeswax. An insect pin (AUSTERLITZ) may be used to pierce two small holes at the second segment of the insect's abdomen where the two abdominal stimulating electrodes (or the first abdominal-electrode insert 166 and the second abdominal-electrode insert 168) may be implanted into. The depth of implant may be 0.5 cm. The implants may be fixed in position with beeswax. The Madagascar hissing cockroach 112 may be given 30 minutes to 1 hour to recover after the implantation.

According to various embodiments, for example in the prototype, stimulation may include bipolar square wave being employed to stimulate the Madagascar hissing cockroach 112. The amplitude of the stimuli may be varied up to 20 Vpp, whereas the frequency may be adjusted from 10 Hz to 50 Hz, depending on individual Madagascar hissing cockroach 112. According to various embodiments, for example in the prototype, a stimulus may be transferred to two left electrodes (or the first cercal-electrode insert 162 and the first abdominal-electrode insert 166) to induce a right turn and vice versa, whereas an electrical stimulation of two cercal electrodes (or the first cercal-electrode insert 162 and the second cercal-electrode insert 164) may elicit a forward acceleration from the Madagascar hissing cockroach 112. Accordingly, electrical stimulus passed to one of the cerci and/or one side of the abdomen may produce a signal of danger making the Madagascar hissing cockroach 112 turning towards the opposite side to escape.

According to various embodiments, for example in the prototype, the success rate based on the above described implantation and stimulation is around 80%. A summary of the parameters of the prototype and the results are tabulated in table 1 below.

TABLE 1

| | Present invention |
|---|---|
| Species | Madagascan hissing cockroach |
| Size | >=7 cm long |
| Gender | Male |
| No. of electrodes | 4 |
| Implantation | Two into two cerci (1 cm depth) Two into two black dots at the back or abdomen region (0.5 cm depth) |
| Electrode material | Coated Platinum Wire: 76.2 μm bare-139.7 μm coated diameter |
| Anesthetize | $CO_2$ gas (Not compulsory) |
| Time to Recover | 30 mins to 1 hour |
| Stimulation Source | Electrical voltage source |
| Stimulation Protocol | Bipolar 4-20 Vpp 10-50 Hz |
| Locomotion control | Steer to left/right using two right/left electrodes respectively Forward motion induced using two cercal electrodes simultaneously |

TABLE 1-continued

| | Present invention |
|---|---|
| Success rate to induce desired motion | 80% |
| Sign of gradual unresponsiveness | No, but there is sign of being tired |

The following describes the method 101 of operating the system 100 for automatic navigation of the hybrid robot 110.

Figure 5:
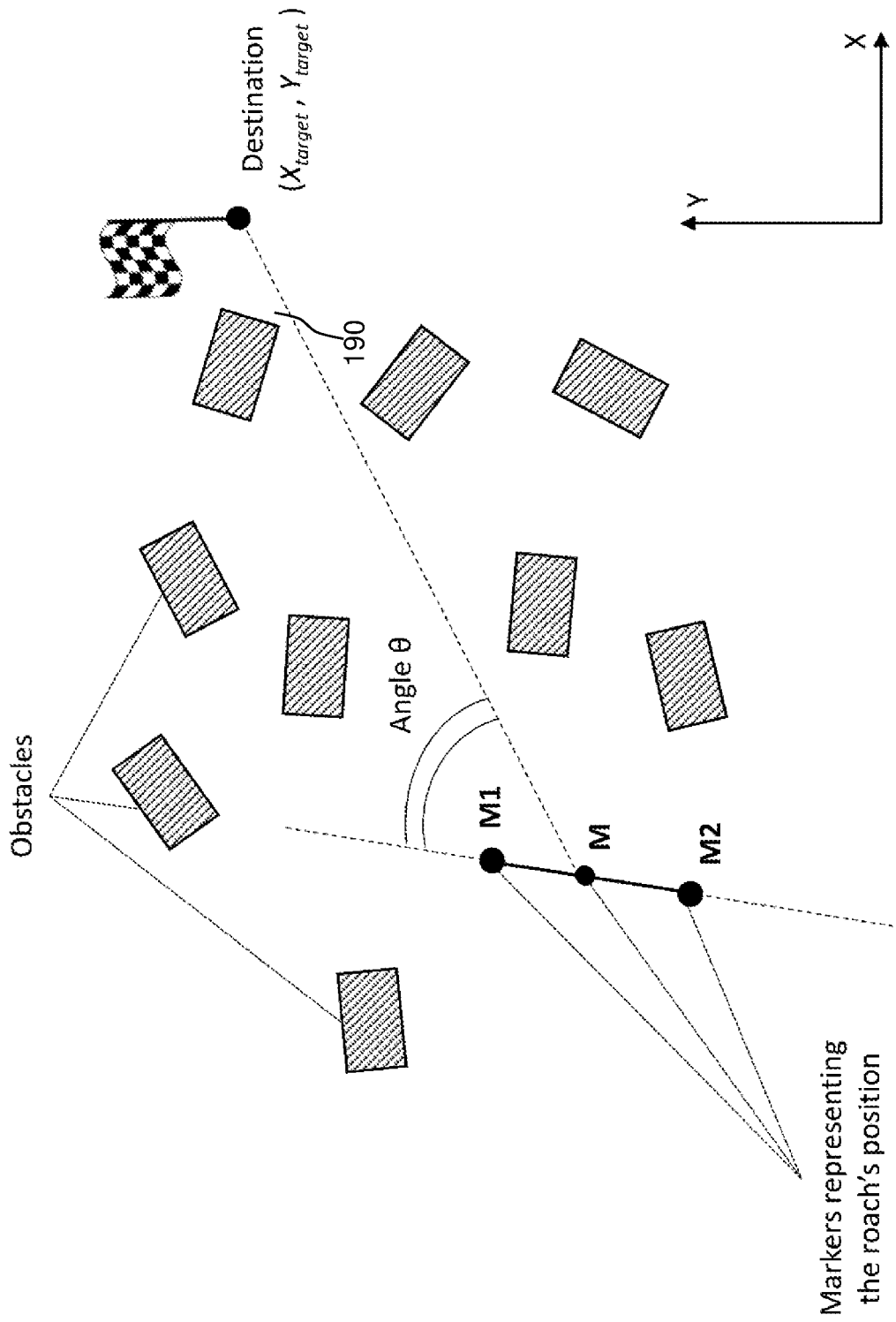
FIG. 5 shows differential orientation of the hybrid robot of FIG. 2 relative to a predetermined destination represented by the angle θ according to various embodiments.

According to various embodiments, the method 101 may include a set of navigational rules established to automatically navigate the hybrid robot 110 from one location to another. According to various embodiments, these rules may be configured to take advantage of two major benefits of employing living animal (for example, terrestrial insects) that includes their own will of moving and their natural capability of obstacle avoidance. According to various embodiments, the set of the navigational rules, thus, may maximize utilization of the animal's (or insect's or Madagascar hissing cockroach's) natural locomotion. By doing so, power consumption efficacy may be greatly attained; in addition, the complexity of the automatic navigation or the necessity of additional sensors to cope with obstructions may be significantly minimized. According to various embodiments, for example in the prototype, the following algorithm or steps in table 2 with reference to FIG. 4 and FIG. 5 may be implemented for the animal-machine hybrid robot 110 as an automatic navigation program to be automatically navigated toward a pre-determined destination 190. FIG. 5 shows the differential orientation of the hybrid robot 110 relative to the predetermined destination 190 representing by the angle θ. According to various embodiments, the automatic navigation program may interpret this angle to issue appropriate locomotion command such as left/right steering or acceleration. The three letters M1, M, M2 may be used to determine the orientation of the hybrid robot 110 as well as the position. According to various embodiments, the algorithm or steps for automatic navigation in table 2 may be programmed into the external processing unit 102 as executable instructions or commands for interacting with the various components (e.g. electric stimulator 150, and/or the positioning component 176, and/or the communication module 174) of the electronic backpack 130 of the arthropod locomotion stimulation device 120 of the hybrid robot 110.

TABLE 2

Step 1: The coordinate of the pre-determined destination 190 may be defined.
Step 2: A localization system (or the positioning component 176 of the electronic backpack 130) periodically may provide the hybrid robot's locational information (e.g. position and orientation). This period of data collection may be termed as the update time interval (see FIG. 4). The distance between the hybrid robot 110 and the target (or pre-determined destination 190) may be computed to issue the arrival judgment. If the hybrid robot 110 does not reach the destination, the automatic navigation program may proceed with Step 3; otherwise, it may be terminated.
Step 3: The angular difference between the hybrid robot's orientation and the pre-determined destination 190 may be calculated (see FIG. 5). There may be two scenarios in which the calculated angle Θ is smaller or bigger than a pre-defined threshold (which may be 25° by default as an example).

| Scenario 1 (Θ ≤ 25°) | Scenario 2 (Θ > 25°) |
|---|---|
| Step 4: The hybrid robot 110 may be judged as facing the destination. It may, thus, be allowed to walk freely by the living animal. | Step 4: The hybrid robot 110 may be steered toward the destination using the electrical stimulation of unilateral electrode pairs (e.g. the pair of the first cercal-electrode insert 162 and the first abdominal-electrode insert 166, or the pair of the second cercal-electrode insert 164 and the second abdominal-electrode insert 168). The steering direction may be |

TABLE 2-continued

| | |
|---|---|
| Step 5: During this free walk, the velocity of the hybrid robot 110 may be monitored or calculated. If the returned value is smaller than 1 cm/s as an example (and which is adjustable), the hybrid robot 110 may be considered as being motionless. It may then be accelerated using the electrical stimulation (e.g. on both cerci). In contrary, If the hybrid robot 110 is in motion, the navigation program may continue looping from Step 2. | selected to minimize the needed angular displacement. Step 5: During the steering process, the duration of the electrical stimulus may be measured. If the hybrid robot's orientation doesn't reach the desired direction (angle $\Theta < 25$) within 5 seconds, the hybrid robot 110 may be recognized to be obstructed (so it cannot turn) and it is accelerated, whereby both cerci may stimulated for inducing forward motion (e.g. by the first cercal-electrode insert 162 and the second cercal-electrode insert 164). The hybrid robot 110 may then be released from the controller (i.e. no stimulation) so as to let it move freely for a defined duration (2 s by default as an example) by the living animal. |
| Step 6: The process may be repeated from Step 2. | |

According to various embodiments, there is provided a system or device for locomotion control including the electronic backpack 130 having the electronic stimulator module (or the electric stimulator 150) connected to four electrodes (or the first cercal-electrode insert 162, the second cercal-electrode insert 164, the first abdominal-electrode insert 166 and the second abdominal-electrode insert 168).

According to various embodiments, the electrodes (or the first cercal-electrode insert 162, the second cercal-electrode insert 164, the first abdominal-electrode insert 166 and the second abdominal-electrode insert 168) may be PFA-coated platinum wires.

According to various embodiments, the electronic backpack 130 may be mountable or mounted onto an animal (or an insect). According to various embodiments, the animal (or the insect) may be a Madagascan hissing cockroach 112. According to various embodiments, the tips of the two cerci of the the insect (or the Madagascan hissing cockroach 112) may be trimmed off to create two small holes for the insertion of electrodes. Similarly, for insertion of electrodes, an insect pin may be used to pierce a small hole on the left and right second segment of the abdomen. According to various embodiments, the electrodes may be inserted into the right cercus, second segment of the right abdomen, left cercus, and second segment of the left abdomen. For example, the first cercal-electrode insert 162 may be inserted into the left cercus, the second cercal-electrode insert 164 may be inserted into the right cercus, the first abdominal-electrode insert 166 may be inserted into the second segment of the left abdomen and the second abdominal-electrode insert 168 may be inserted into the second segment of the right abdomen. According to various embodiments, the inserted electrodes may be fixed in position using beeswax.

According to various embodiments, the stimulator module (or the electric stimulator 150) may be configured to produce bipolar square wave electrical stimuli, with amplitudes in the range from up to 20 Vpp, and frequencies in the range of 10 Hz to 50 Hz, depending on the insect (or the Madagascan hissing cockroach 112). According to various embodiments, providing electrical stimulation to the right side (i.e., right cercus and right abdomen) may make the arthropod (or the insect or the Madagascan hissing cockroach 112) turn left, providing electrical stimulation to the left side (i.e., left cercus and left abdomen) may make the arthropod (or the insect or the Madagascan hissing cockroach 112) turn right and providing stimulation to just the two cerci may make the arthropod (or the insect or the Madagascan hissing cockroach 112) accelerate forward.

According to various embodiments, the electronic backpack 130 may further include a localization component (or positioning component 176) having an accelerometer or an inertial measurement unit (IMU) or a global/indoor positioning system (GPS) unit or an indoor positioning system (IPS) unit or combination thereof. According to various embodiments, the localization component (or positioning component 176) may be used to detect and generate locational information, such as position and/or orientation and/or displacement and/or velocity and/or acceleration, of the hybrid robot 110 during operation. According to various embodiments, the electronic backpack 130 may further include a wireless data transmission module (or communication module 174) for transmitting the locational information to a remote server or control center.

According to various embodiments, the system 100 may further include a feedback control system (e.g. the automatic navigation program) having a set of navigational rules for controlling or regulating the hybrid robot's movement so that it travels along a pre-determined path to the pre-determined destination 190. The feedback control system may be provided on the external processing unit 102 (e.g. a remote server or a control center). According to various embodiments, the set of navigational rules may be based on the locational information of the hybrid robot 110 and a coordinate of the pre-determined destination 190. According to various embodiments, the set of navigational rules may be further based on an angular difference between the hybrid robot's orientation and the pre-determined destination 190, and a pre-defined angular difference threshold. According to various embodiments, the set of navigational rules may be configured to allow free movement of the hybrid robot 110 by the animal (or insect) when the angular difference is within the pre-defined angular difference threshold, and to control or regulate the hybrid robot's movement when the angular difference exceeds the pre-defined angular difference threshold. Further, the set of navigational rules may be configured to determine whether the hybrid robot 110 is obstructed based on whether the one or the combination of the displacement, the velocity or the acceleration of the hybrid robot 110 in response to a stimulus is less than the pre-defined minimum displacement, the pre-defined minimum velocity or the pre-defined minimum acceleration respectively.

The following pertain to various embodiments.

According to various embodiments, there is provided a method of controlling a movement of a hybrid robot including a locomotion stimulation device carried by an animal, the method including:

monitoring, via a positioning component of an electronic backpack of the locomotion stimulation device of the hybrid robot, a position and an orientation (or angular position) of the electronic backpack of the locomotion stimulation device as a measure of a position and an orientation (or angular position) of the hybrid robot;

providing, via a stimulator of the electronic backpack of the locomotion stimulation device, a stimulus to the animal based on an angular difference between the orientation of the electronic backpack of the locomotion stimulation device with respect to a direct path from the position of the electronic backpack to a predetermined destination for stimulating the animal to move in a desired manner so as to control the movement of the hybrid robot;

monitoring, via the positioning component of the electronic backpack of the locomotion stimulation device of the hybrid robot, any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal; and ceasing provision of the stimulus to the animal from the stimulator of the electronic backpack of the locomotion stimulation device in response to the corresponding one or the combination of the displacement, the velocity or the acceleration of the motion of the hybrid robot being below a pre-defined minimum displacement, a pre-defined minimum velocity or a pre-defined minimum acceleration respectively in a manner so as to allow the animal to roam freely.

According to various embodiments, the method may optionally include that providing the stimulus to the animal may include providing a forward stimulus for stimulating movement in a forward direction when the angular difference is equal or less than a pre-defined threshold.

According to various embodiments, the method may optionally include that monitoring the one or the combination of the displacement, the velocity or the acceleration of the electronic backpack of the locomotion stimulation device may include monitoring a corresponding one or a combination of a linear displacement, a linear velocity or a linear acceleration of the electronic backpack of the locomotion stimulation device, and wherein the pre-defined minimum displacement, the pre-defined minimum velocity or the pre-defined minimum acceleration may be a pre-defined minimum linear displacement, a pre-defined minimum linear velocity or a pre-defined minimum linear acceleration.

According to various embodiments, the method may optionally include that providing stimulus to the animal may include providing a right-turn stimulus for stimulating turning to a right direction or a left-turn stimulus for stimulating turning to a left direction when the angular difference is greater than a pre-defined threshold.

According to various embodiments, the method may optionally include that monitoring the one or the combination of the displacement, the velocity or the acceleration of the electronic backpack of the locomotion stimulation device may include monitoring a corresponding one or a combination of an angular displacement, an angular velocity or an angular acceleration of the electronic backpack of the locomotion stimulation device, and wherein the pre-defined minimum displacement, the pre-defined minimum velocity or the pre-defined minimum acceleration may be a pre-defined minimum angular displacement, a pre-defined minimum angular velocity or a pre-defined minimum angular acceleration.

According to various embodiments, the method may optionally include that monitoring the position and the orientation of the electronic backpack of the locomotion stimulation device may be resumed after a predetermined period of time of ceasing provision of the stimulus to the animal.

According to various embodiments, the method may optionally include, in response to the corresponding one or the combination of the displacement, the velocity or the acceleration of the motion of the hybrid robot being below the pre-defined minimum displacement, the pre-defined minimum velocity or the pre-defined minimum acceleration respectively, providing an acceleration stimulus, via the stimulator of the electronic backpack of the locomotion stimulation device, to induce acceleration of the animal after ceasing provision of the stimulus to the animal; and ceasing provision of the acceleration stimulus to the animal from the stimulator of the electronic backpack of the locomotion stimulation device after a first predetermined period of time of providing the acceleration stimulus; and wherein monitoring the position and orientation of the electronic backpack of the locomotion stimulation device may be resumed after a second predetermined period of time of ceasing provision of the acceleration stimulus to the animal.

According to various embodiments, the method may optionally include that, wherein the hybrid robot is part of an animal locomotion control system, monitoring the position and the orientation of the electronic backpack of the locomotion stimulation device may include determining, via a processing unit of the animal locomotion control system, the angular difference between the orientation of the electronic backpack of the locomotion stimulation device with respect to the direct path from the position of the electronic backpack to the predetermined destination.

According to various embodiments, the method may optionally include that providing the stimulus to the animal may include determining, via the processing unit of the animal locomotion control system, a stimulation control signal to be sent to the electronic backpack of the locomotion control device based on the angular difference for controlling the stimulator of the electronic backpack of the locomotion stimulation device to provide the stimulus to the animal, and sending the stimulation control signal from the processing unit of the animal locomotion control system to the stimulator of the electronic backpack of the locomotion stimulation device.

According to various embodiments, the method may optionally include that monitoring the one or the combination of the displacement, the velocity or the acceleration of the electronic backpack of the locomotion stimulation device may include sending the one or the combination of the displacement, the velocity or the acceleration of the electronic backpack of the locomotion stimulation device obtained from the positioning component of the electronic backpack of the locomotion stimulation device to the processing unit of the animal locomotion control system.

According to various embodiments, the method may optionally include that monitoring the one or the combination of the displacement, the velocity or the acceleration of the electronic backpack of the locomotion stimulation device may further include comparing, via the processing unit of the animal locomotion control system, the one or the combination of the displacement, the velocity or the acceleration of the electronic backpack of the locomotion stimulation device with the pre-defined minimum displacement, the pre-defined minimum velocity or the pre-defined minimum acceleration respectively.

According to various embodiments, the method may optionally include that ceasing provision of the stimulus to the animal from the stimulator of the electronic backpack of the locomotion stimulation device may include sending, via the processing unit of the animal locomotion control system, a cease-stimulation control signal from the processing unit of the animal locomotion control system to the stimulator of the electronic backpack of the locomotion stimulation device when the one or the combination of the displacement, the velocity or the acceleration of the electronic backpack of the locomotion stimulation device is less than the pre-defined minimum displacement, the pre-defined minimum velocity or the pre-defined minimum acceleration respectively.

According to various embodiments, the method may optionally include that providing the acceleration stimulus to induce acceleration of the animal may include sending an acceleration stimulation control signal from the processing unit of the animal locomotion control system to the stimulator of the electronic backpack of the locomotion stimulation device.

According to various embodiments, the method may optionally include that ceasing provision of the acceleration stimulus to the animal from the stimulator of the electronic backpack of the locomotion stimulation device after the first predetermined period of time of providing the acceleration stimulus may optionally include sending, via the processing unit of the animal locomotion control system, a cease-acceleration stimulation control signal from the processing unit of the animal locomotion control system to the stimulator of the electronic backpack of the locomotion stimulation device after the first predetermined period of time of providing the acceleration stimulus.

According to various embodiments, the method may optionally include that monitoring the position and the orientation of the electronic backpack of the locomotion stimulation device may be resumed when the one or the combination of the displacement, the velocity or the acceleration of the motion of the hybrid robot is equal or greater than the pre-defined minimum displacement, the pre-defined minimum velocity or the pre-defined minimum acceleration respectively.

According to various embodiments, there is provided an animal locomotion control system for controlling a movement of a hybrid robot using an animal as a legged platform, the locomotion stimulation control system including:
    a locomotion stimulation device carriable by the animal,
        the locomotion stimulation device including
            an electronic backpack including
                a support structure,
                a positioning component coupled to the support structure, and
                a stimulator coupled to the support structure, and
                at least a pair of electrodes for direct contact with a body part of the animal, the at least a pair of electrodes being connected to the stimulator; and
    a processing unit in communication with the locomotion stimulation device,
    wherein the positioning component of the electronic backpack of the locomotion stimulation device is configured to monitor a position and an orientation of the electronic backpack of the locomotion stimulation device as a measure of a position and an orientation of the hybrid robot,
    wherein the processing unit is configured to determine an angular difference between the orientation of the electronic backpack of the locomotion stimulation device with respect to the direct path from the position of the electronic backpack to the predetermined destination,
    wherein the stimulator of the electronic backpack of the locomotion stimulation device is configured to provide a stimulus to the animal based on the angular difference determined by the processing unit,
    wherein the positioning component is further configured to monitor any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal, and
wherein the stimulator of the electronic backpack of the locomotion stimulation device is configured to cease providing the stimulus to the animal in response to the corresponding one or the combination of the displacement, the velocity or the acceleration of the motion of the hybrid robot being below a pre-defined minimum displacement, a pre-defined minimum velocity or a pre-defined minimum acceleration respectively such that the animal roam freely According to various embodiments, the system may optionally include that the stimulator of the electronic backpack of the locomotion device may be configured to provide a forward stimulus for stimulating movement in a forward direction when the angular difference determined by the processing unit is equal or less than a pre-defined threshold.

According to various embodiments, the system may optionally include that the one or the combination of the displacement, the velocity or the acceleration of the electronic backpack of the locomotion stimulation device monitored by the positioning component may be a corresponding one or a combination of a linear displacement, a linear velocity or a linear acceleration of the electronic backpack of the locomotion stimulation device, and wherein the pre-defined minimum displacement, the pre-defined minimum velocity or the pre-defined minimum acceleration may be a pre-defined minimum linear displacement, a pre-defined minimum linear velocity or a pre-defined minimum linear acceleration.

According to various embodiments, the system may optionally include that the stimulator of the electronic backpack of the locomotion device may be configured to provide a right-turn stimulus for stimulating turning to a right direction or a left-turn stimulus for stimulating turning to a left direction when the angular difference determined by the processing unit is greater than a pre-defined threshold.

According to various embodiments, the system may optionally include that the one or the combination of the displacement, the velocity or the acceleration of the electronic backpack of the locomotion stimulation device monitored by the positioning component may be a corresponding one or a combination of an angular displacement, an angular velocity or an angular acceleration of the electronic backpack of the locomotion stimulation device, and wherein the pre-defined minimum displacement, the pre-defined minimum velocity or the pre-defined minimum acceleration may be a pre-defined minimum angular displacement, a pre-defined minimum angular velocity or a pre-defined minimum angular acceleration.

According to various embodiments, the system may optionally include that the positioning unit of the electronic backpack of the locomotion device may be configured to resume monitoring of the position and the orientation of the electronic backpack of the locomotion stimulation device after the stimulator of the electronic backpack of the locomotion device ceases providing the stimulus to the animal for a predetermined period of time.

According to various embodiments, the system may optionally include that, in response to the corresponding one or the combination of the displacement, the velocity or the acceleration of the motion of the hybrid robot being below the pre-defined minimum displacement, the pre-defined minimum velocity or the pre-defined minimum acceleration respectively, the stimulator of the electronic backpack of the locomotion stimulation device may be further configured to provide an acceleration stimulus to induce acceleration of the animal after ceasing provision of the stimulus to the animal and to cease provision of the acceleration stimulus to the animal after a first predetermined period of time of providing the acceleration stimulus, and wherein the positioning unit of the electronic backpack of the locomotion device may be configured to resume monitoring of the position and the orientation of the electronic backpack of the locomotion stimulation device after the stimulator of the electronic backpack of the locomotion device ceases providing the acceleration stimulus to the animal for a second predetermined period of time.

According to various embodiments, the system may optionally include that the processing unit of the animal locomotion control system may be configured to send a stimulation control signal to the electronic backpack of the locomotion control device based on the angular difference determined so as to control the stimulator of the electronic backpack of the locomotion stimulation device to provide the stimulus to the animal.

According to various embodiments, the system may optionally include that the processing unit of the animal locomotion control system may be configured to compare the one or the combination of the displacement, the velocity or the acceleration of the electronic backpack of the locomotion stimulation device with the pre-defined minimum displacement, the pre-defined minimum velocity or the pre-defined minimum acceleration respectively and send a cease-stimulation control signal to the stimulator of the electronic backpack of the locomotion stimulation device when the one or the combination of the displacement, the velocity or the acceleration of the electronic backpack of the locomotion stimulation device is less than the pre-defined minimum displacement, the pre-defined minimum velocity or the pre-defined minimum acceleration respectively.

According to various embodiments, the system may optionally include that the processing unit of the animal locomotion control system may be configured to send an acceleration stimulation control signal to the stimulator of the electronic backpack of the locomotion stimulation device after sending the cease-stimulation control signal.

According to various embodiments, the system may optionally include that the processing unit of the animal locomotion control system may be configured to send a cease-acceleration stimulation control signal to the stimulator of the electronic backpack of the locomotion stimulation device after the first predetermined period of time.

According to various embodiments, the system may optionally include that the stimulator of the electronic backpack may include an electric stimulator.

According to various embodiments, the system may optionally include that the electric stimulator of the electronic backpack may include a voltage source to generate a voltage waveform output signal to be transmitted to the at least one electrode.

According to various embodiments, the system may optionally include that the electronic backpack may include one or more task-specific components coupled to the support structure.

According to various embodiments, the system may optionally include that the electronic backpack may include a communication module to connect with the processing unit via a wired or wireless communication, the communication module being coupled to the support structure.

According to various embodiments, the system may optionally include that the positioning component may include an inertial measurement unit.

According to various embodiments, the system may optionally include that the positioning component may include a tracking unit of a global navigation satellite system, a global positioning system, a local positioning system, or an indoor positioning system.

According to various embodiments, the system may optionally include one or more positioning reference units from which the positioning component of the locomotion control device determines the position of the electronic backpack via position fixing methods, wherein the positioning component of the locomotion control device and the one or more positioning reference units form a positioning system.

According to various embodiments, there is provided an arthropod locomotion stimulation device including:
an electronic backpack having a fore-and-aft axis to define a forward direction as being extending outward from a forward end of the electronic backpack along the fore-and-aft axis and a rearward direction as being extending outward from a rear end of the electronic backpack along the fore-and-aft axis, and a transverse axis across the fore-and-aft axis to define a left direction as being extending perpendicularly away from the fore-and-aft axis along the transverse axis on a left side of the fore-and-aft axis with respect to the forward direction and a right direction as being extending perpendicularly away from the fore-and-aft axis along the transverse axis on a right side of the fore-and-aft axis with respect to the forward direction, wherein the electronic backpack includes
a support structure, and
an electric stimulator coupled to the support structure;
a first cercal-electrode insert and a second cercal-electrode insert in a spaced apart side-by-side arrangement with the first cercal-electrode insert being on the left side of the fore-and-aft axis by a first predetermined perpendicular distance and the second cercal-electrode insert being on the right side of the fore-and-aft axis by the same first predetermined perpendicular distance, wherein the first cercal-electrode insert and the second cercal-electrode insert are respectively disposed at predetermined positions with a predetermined rearward distance in the rearward direction apart from the rear end of the electronic backpack; and a first abdominal-electrode insert and a second abdominal-electrode insert in a spaced apart side-by-side arrangement with the first abdominal-electrode inset being on the left side of the fore-and-aft axis by a second predetermined perpendicular distance and the second abdominal-electrode insert being on the right side of the fore-and-aft axis by the same second predetermined perpendicular distance, wherein the first abdominal-electrode insert and the second abdominal-electrode insert are located between the forward end of the electronic backpack and the predetermined positions of the first cercal-electrode insert and the second cercal-electrode insert, wherein each of the first cercal-electrode insert, the second cercal-electrode insert, the first abdominal-electrode insert and the second abdominal-electrode insert are electrically connected to the electric stimulator of the electronic backpack.

According to various embodiments, the arthropod locomotion stimulation device may optionally include that each of the first cercal-electrode insert, the second cercal-electrode insert, the first abdominal-electrode insert and the second abdominal-electrode insert may include a platinum wire.

According to various embodiments, the arthropod locomotion stimulation device may optionally include that the electric stimulator of the electronic backpack may be configured to include one or a combination of the following stimulation modes including a first electric stimulation mode wherein the electric stimulator is operable to provide a first electric stimulus via the first cercal-electrode insert and the second cercal-electrode insert for stimulating movement in the forward direction, a second electric stimulation mode wherein the electric stimulator is operable to provide a second electric stimulus via the first cercal-electrode insert and the first abdominal-electrode insert for stimulating turning to the right direction, and a third electric stimulation mode wherein the electric stimulator is operable to provide a third electric stimulus via the second cercal-electrode insert and the second abdominal-electrode insert for controlling turning to the left direction.

According to various embodiments, the arthropod locomotion stimulation device may optionally include that the electric stimulator may include a voltage source to generate a voltage waveform output signal to be transmitted to one or a pair or a combination of the first cercal-electrode insert, the second cercal-electrode insert, the first abdominal-electrode insert or the second abdominal-electrode insert.

According to various embodiments, the arthropod locomotion stimulation device may optionally include that, when in the first electric stimulation mode, the electric stimulator of the electronic backpack may transmit the voltage waveform output signal serving as the first electric stimulus to the first cercal-electrode insert and the second cercal-electrode insert. According to various embodiments, the arthropod locomotion stimulation device may optionally include that, when operating in the second electric stimulation mode, the electric stimulator of the electronic backpack may transmit the voltage waveform output signal serving as the second electric stimulus to the first cercal-electrode insert and the first abdominal-electrode insert. According to various embodiments, the arthropod locomotion stimulation device may optionally include that, when operating in the third electric stimulation mode, the electric stimulator of the electronic backpack may transmit the voltage waveform output signal serving as the third electric stimulus to the second cercal-electrode insert and the second abdominal-electrode insert.

According to various embodiments, the arthropod locomotion stimulation device may optionally include that the voltage waveform output signal may include a bipolar square wave having a peak to peak voltage (Vpp) in a range of 4 V to 20 V and a frequency in a range of 10 Hz to 50 Hz.

According to various embodiments, the arthropod locomotion stimulation device may optionally include that the second predetermined perpendicular distance may be greater than the first predetermined perpendicular distance.

According to various embodiments, the arthropod locomotion stimulation device may optionally include that the electronic backpack may further include one or more task-specific components coupled to the support structure.

According to various embodiments, the arthropod locomotion stimulation device may optionally include that the electronic backpack may further include a communication module to connect with an external processing unit via a wired or wireless communication, the communication module being coupled to the support structure.

According to various embodiments, the arthropod locomotion stimulation device may optionally include that the electronic backpack may further include a positioning component to determine a position, an orientation, and one or a combination of a displacement, a velocity, or an acceleration of the electronic backpack, the positioning component being coupled to the support structure.

According to various embodiments, the arthropod locomotion stimulation device may optionally include that the positioning component may include an inertial measurement unit.

According to various embodiments, there is provided an arthropod locomotion control system including:

the arthropod locomotion control device as described herein; and the external processing unit, wherein the positioning component of the electronic backpack of the arthropod locomotion control device is configured to determine the position and the orientation of the electronic backpack with respect to the operating space of the arthropod locomotion control device, wherein the communication module of the electronic backpack of the arthropod locomotion control device is configured to send the position and the orientation of the electronic backpack to the external processing unit, wherein the external processing unit is configured to determine a stimulation control signal to be sent to the electronic backpack of the arthropod locomotion control device based on comparing the position and orientation of the electronic backpack and a predetermined destination of the electronic backpack within the operating space of the arthropod locomotion control device, wherein the communication module of the electronic backpack of the arthropod locomotion control device is configured to receive the stimulation control signal from the external processing unit, and wherein the electric stimulator of the electronic backpack of the arthropod locomotion control device is operated based on the stimulation control signal from the external processing unit.

According to various embodiments, the system may further include one or more positioning reference units from which the positioning component of the arthropod locomotion control device determines the position of the electronic backpack with respect to the operating space of the arthropod locomotion control device via position fixing methods, wherein the positioning component of the arthropod locomotion control device and the one or more positioning reference units form a positioning system. According to various embodiment, the system may optionally include that, the positioning system may include a global navigation satellite system, a global positioning system, a local positioning system, or an indoor positioning system.

According to various embodiments, there is provided a method of operating the arthropod locomotion control system as described herein, the method including:
- determining, via the positioning component of the electronic backpack of the arthropod locomotion control device, the position and the orientation of the electronic backpack with respect to the operating space of the arthropod locomotion control device;
- determining, via the external processing unit, the stimulation control signal to be sent to the electronic backpack of the arthropod locomotion control device based on comparing the position and the orientation of the electronic backpack and the predetermined destination of the electronic backpack within the operating space of the arthropod locomotion control device; and
- operating the electric stimulator of the electronic backpack of the arthropod locomotion control device to provide a stimulus based on the stimulation control signal.

According to various embodiments, the method may optionally include that determining the position and orientation of the electronic backpack with respect to the operating space of the arthropod locomotion control device is resumed or repeated after a predetermined fixed interval of no stimulus provided by the electric stimulator of the electronic backpack.

According to various embodiments, the method may optionally include that determining the stimulation control signal to be sent may further include,
- determining an angular difference between the orientation of the electronic backpack with respect to a direct path from the position of the electronic backpack to the predetermined destination within the operating space of the arthropod locomotion control device.

According to various embodiments, the method may optionally include that determining the stimulation control signal to be sent may further include, sending a steering stimulation control signal to steer the arthropod locomotion control device when the angular difference is greater than a pre-defined threshold.

According to various embodiments, the method may optionally include that determining the stimulation control signal to be sent may further include,
- sending, via the external processing unit, the steering stimulation control signal to the electric stimulator of the electronic backpack of the arthropod locomotion control device for steering;
- monitoring, via the positioning component, any one or a combination of a displacement, a velocity or an acceleration of the electronic backpack of the arthropod locomotion stimulation device in response to a steering stimulus provided by the stimulator of the electronic backpack of the arthropod locomotion stimulation device based on the steering stimulation control signal; and
- ceasing provision of the steering stimulus from the stimulator of the electronic backpack of the arthropod locomotion stimulation device in response to the one or the combination of the displacement, the velocity or the acceleration of the electronic backpack of the arthropod locomotion stimulation device being below a pre-defined minimum displacement, a pre-defined minimum velocity or a pre-defined minimum acceleration respectively.

According to various embodiments, the method may optionally include that monitoring the one or the combination of the displacement, the velocity or the acceleration of the electronic backpack of the arthropod locomotion stimulation device may include monitoring a corresponding one or a combination of an angular displacement, an angular velocity or an angular acceleration of the electronic backpack of the arthropod locomotion stimulation device, and wherein the pre-defined minimum displacement, the pre-defined minimum velocity or the pre-defined minimum acceleration may be a pre-defined minimum angular displacement, a pre-defined minimum angular velocity or a pre-defined minimum angular acceleration.

According to various embodiments, the method may optionally include that determining the stimulation control signal to be sent may further include,
- sending, via the processing unit, a cease-stimulation control signal from the processing unit to the electric stimulator of the electronic backpack of the arthropod locomotion stimulation device when the one or the combination of the displacement, the velocity or the acceleration of the electronic backpack of the arthropod locomotion stimulation device is less than the pre-defined minimum displacement, the pre-defined minimum velocity or the pre-defined minimum acceleration respectively.

According to various embodiments, the method may optionally include that determining the position and the orientation of the electronic backpack of the arthropod locomotion stimulation device may be resumed after a predetermined period of time of ceasing provision of the steering stimulus form the electric stimulator of the electronic backpack of the arthropod locomotion stimulation device.

According to various embodiments, the method may optionally include, in response to the one or the combination of the displacement, the velocity or the acceleration of the electronic backpack of the arthropod locomotion stimulation device being below the pre-defined minimum displacement, the pre-defined minimum velocity or the pre-defined minimum acceleration respectively, providing an acceleration stimulus, via the electric stimulator of the electronic backpack of the arthropod locomotion stimulation device, to induce acceleration after ceasing provision of the steering stimulus; and ceasing provision of the acceleration stimulus from the stimulator of the electronic backpack of the arthropod locomotion stimulation device after a first predetermined period of time of providing the acceleration stimulus, and wherein determining the position and orientation of the electronic backpack of the arthropod locomotion stimulation device is resumed after a second predetermined period of time of ceasing provision of the acceleration stimulus.

According to various embodiments, the method may optionally include that providing the acceleration stimulus to induce acceleration may include sending an acceleration stimulation control signal from the external processing unit to the stimulator of the electronic backpack of the arthropod locomotion stimulation device.

According to various embodiments, the method may optionally include that ceasing provision of the acceleration stimulus from the electric stimulator of the electronic backpack of the arthropod locomotion stimulation device after the first predetermined period of time of providing the acceleration stimulus may include sending, via the external processing unit, a cease-acceleration stimulation control signal from the external processing unit to the electric stimulator of the electronic backpack of the arthropod locomotion stimulation device after the first predetermined period of time of providing the acceleration stimulus.

According to various embodiments, the method may optionally include that determining the position and the orientation of the electronic backpack of the arthropod locomotion stimulation device may be resumed when the one or the combination of the displacement, the velocity or the acceleration of the motion of the hybrid robot is equal or greater than the pre-defined minimum displacement, the pre-defined minimum velocity or the pre-defined minimum acceleration respectively.

Various embodiments have provided a method of controlling a movement of a hybrid robot, an animal locomotion stimulation system for controlling a movement of a hybrid robot, a locomotion stimulation device, and a method of operating the arthropod locomotion control system for manipulating the animal (or insect) by electrically stimulating their muscles and/or sensory which may require much less power than that for conventional man-made small-legged robots. Various embodiments are capable of utilizing the living animal (or insect) as legged platform for motion as well as for traversing obstacles naturally without requiring complicated algorithms.

While the invention has been particularly shown and described with reference to specific embodiments, it should be understood by those skilled in the art that various changes, modification, variation in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. A method of controlling a movement of a hybrid robot comprising a locomotion stimulation device carried by an animal, the method comprising:
monitoring, via a positioning component of an electronic backpack of the locomotion stimulation device of the hybrid robot, a position and an orientation of the electronic backpack of the locomotion stimulation device as a measure of a position and an orientation of the hybrid robot;
providing, via a stimulator of the electronic backpack of the locomotion stimulation device, a stimulus to the animal based on an angular difference between the orientation of the electronic backpack of the locomotion stimulation device with respect to a direct path from the position of the electronic backpack to a predetermined destination for stimulating the animal to move in a desired manner so as to control the movement of the hybrid robot;
monitoring, via the positioning component of the electronic backpack of the locomotion stimulation device of the hybrid robot, any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal; and ceasing provision of the stimulus to the animal from the stimulator of the electronic backpack of the locomotion stimulation device in response to the corresponding one or the combination of the displacement, the velocity or the acceleration of the motion of the hybrid robot being below a pre-defined minimum displacement, a pre-defined minimum velocity or a pre-defined minimum acceleration respectively in a manner-se as to allow the animal to roam freely.

2. The method as claimed in claim 1, wherein providing the stimulus to the animal comprises providing a forward stimulus for stimulating movement in a forward direction when the angular difference is equal or less than a pre-defined threshold,
wherein monitoring the one or the combination of the displacement, the velocity or the acceleration of the electronic backpack of the locomotion stimulation device comprises monitoring a corresponding one or a combination of a linear displacement, a linear velocity or a linear acceleration of the electronic backpack of the locomotion stimulation device, and wherein the pre-defined minimum displacement, the pre-defined minimum velocity or the pre-defined minimum acceleration is a pre-defined minimum linear displacement, a pre-defined minimum linear velocity or a pre-defined minimum linear acceleration.

3. The method as claimed in claim 1, wherein providing stimulus to the animal comprises providing a right-turn stimulus for stimulating turning to a right direction or a left-turn stimulus for stimulating turning to a left direction when the angular difference is greater than a pre-defined threshold,
wherein monitoring the one or the combination of the displacement, the velocity or the acceleration of the electronic backpack of the locomotion stimulation device comprises monitoring a corresponding one or a combination of an angular displacement, an angular velocity or an angular acceleration of the electronic backpack of the locomotion stimulation device, and wherein the pre-defined minimum displacement, the pre-defined minimum velocity or the pre-defined minimum acceleration is a pre-defined minimum angular displacement, a pre-defined minimum angular velocity or a pre-defined minimum angular acceleration.

4. The method as claimed in claim 1, wherein monitoring the position and the orientation of the electronic backpack of the locomotion stimulation device resumes after a predetermined period of time of ceasing provision of the stimulus to the animal.

5. The method as claimed in claim 3, further comprising, in response to the corresponding one or the combination of the displacement, the velocity or the acceleration of the motion of the hybrid robot being below the pre-defined minimum displacement, the pre-defined minimum velocity or the pre-defined minimum acceleration respectively, providing an acceleration stimulus for a first predetermined period of time, via the stimulator of the electronic backpack of the locomotion stimulation device, to induce acceleration of the animal after ceasing provision of the right-turn stimulus or the left-turn stimulus to the animal, and ceasing provision of the acceleration stimulus for a second predetermined period of time to the animal from the stimulator of the electronic backpack of the locomotion stimulation device after the first predetermined period of time of providing the acceleration stimulus, and wherein monitoring the position and orientation of the electronic backpack of the locomotion stimulation device resumes after the second predetermined period of time of ceasing provision of the acceleration stimulus to the animal.

6. The method as claimed in claim 5, wherein the hybrid robot is part of an animal locomotion control system, and wherein monitoring the position and the orientation of the electronic backpack of the locomotion stimulation device comprises determining, via a processing unit of the animal locomotion control system, the angular difference between the orientation of the electronic backpack of the locomotion stimulation device with respect to the direct path from the position of the electronic backpack to the predetermined destination, wherein providing the stimulus to the animal comprises determining, via the processing unit of the animal locomotion control system, a stimulation control signal to be sent to the electronic backpack of the locomotion stimulation device based on the angular difference for controlling the stimulator of the electronic backpack of the locomotion stimulation device to provide the stimulus to the animal, and sending the stimulation control signal from the processing unit of the animal locomotion control system to the stimulator of the electronic backpack of the locomotion stimulation device.

7. The method as claimed in claim 6, wherein monitoring the one or the combination of the displacement, the velocity or the acceleration of the electronic backpack of the locomotion stimulation device comprises sending the one or the combination of the displacement, the velocity or the acceleration of the electronic backpack of the locomotion stimulation device obtained from the positioning component of the electronic backpack of the locomotion stimulation device to the processing unit of the animal locomotion control system, and comparing, via the processing unit of the animal locomotion control system, the one or the combination of the displacement, the velocity or the acceleration of the electronic backpack of the locomotion stimulation device with the pre-defined minimum displacement, the pre-defined minimum velocity or the pre-defined minimum acceleration respectively.

8. The method as claimed in claim 7, wherein ceasing provision of the stimulus to the animal from the stimulator of the electronic backpack of the locomotion stimulation device comprises sending, via the processing unit of the animal locomotion control system, a cease-stimulation control signal from the processing unit of the animal locomotion control system to the stimulator of the electronic backpack of the locomotion stimulation device when the one or the combination of the displacement, the velocity or the acceleration of the electronic backpack of the locomotion stimulation device is less than the pre-defined minimum displacement, the pre-defined minimum velocity or the pre-defined minimum acceleration respectively.

9. The method as claimed in claim 8, wherein providing the acceleration stimulus for the first predetermined period of time to induce acceleration of the animal comprises sending an acceleration stimulation control signal from the processing unit of the animal locomotion control system to the stimulator of the electronic backpack of the locomotion stimulation device.

10. The method as claimed in claim 9, wherein ceasing provision of the acceleration stimulus for the second predetermined period of time to the animal from the stimulator of the electronic backpack of the locomotion stimulation device after the first predetermined period of time of providing the acceleration stimulus comprises sending, via the processing unit of the animal locomotion control system, a cease-acceleration stimulation control signal from the processing unit of the animal locomotion control system to the stimulator of the electronic backpack of the locomotion stimulation device after the first predetermined period of time of providing the acceleration stimulus.

11. The method as claimed in claim 1, wherein monitoring the position and the orientation of the electronic backpack of the locomotion stimulation device resumes when the one or the combination of the displacement, the velocity or the acceleration of the motion of the hybrid robot is equal or greater than the pre-defined minimum displacement, the pre-defined minimum velocity or the pre-defined minimum acceleration respectively.

12. An animal locomotion control system for controlling a movement of a hybrid robot using an animal as a legged platform, the animal locomotion control system comprising:

a locomotion stimulation device carriable by the animal, the locomotion stimulation device comprising
an electronic backpack comprising
a support structure,
a positioning component coupled to the support structure, and
a stimulator coupled to the support structure, and
at least a pair of electrodes for direct contact with a body part of the animal, the at least a pair of electrodes being connected to the stimulator; and a processing unit in communication with the locomotion stimulation device, wherein the positioning component of the electronic backpack of the locomotion stimulation device is configured to monitor a position and an orientation of the electronic backpack of the locomotion stimulation device as a measure of a position and an orientation of the hybrid robot, wherein the processing unit is configured to determine an angular difference between the orientation of the electronic backpack of the locomotion stimulation device with respect to the direct path from the position of the electronic backpack to the predetermined destination, wherein the stimulator of the electronic backpack of the locomotion stimulation device is configured to provide a stimulus to the animal based on the angular difference determined by the processing unit, wherein the positioning component is further configured to monitor any one or a combination of a displacement, a velocity or an acceleration of the electronic backpack of the locomotion stimulation device as a measure of a corresponding one or a combination of a displacement, a velocity or an acceleration of a motion of the hybrid robot in response to the stimulus provided to the animal, and wherein the stimulator of the electronic backpack of the locomotion stimulation device is configured to cease providing the stimulus to the animal in response to the corresponding one or the combination of the displacement, the velocity or the acceleration of the motion of the hybrid robot being below a pre-defined minimum displacement, a pre-defined minimum velocity or a pre-defined minimum acceleration respectively such that the animal roams freely.

13. The system as claimed in claim 12, wherein the stimulator of the electronic backpack of the locomotion device is configured to provide a forward stimulus for stimulating movement in a forward direction when the angular difference determined by the processing unit is equal or less than a pre-defined threshold,
   wherein the one or the combination of the displacement, the velocity or the acceleration of the electronic backpack of the locomotion stimulation device monitored by the positioning component is a corresponding one or a combination of a linear displacement, a linear velocity or a linear acceleration of the electronic backpack of the locomotion stimulation device, and wherein the pre-defined minimum displacement, the pre-defined minimum velocity or the pre-defined minimum acceleration is a pre-defined minimum linear displacement, a pre-defined minimum linear velocity or a pre-defined minimum linear acceleration.

14. The system as claimed in claim 12, wherein the stimulator of the electronic backpack of the locomotion device is configured to provide a right-turn stimulus for stimulating turning to a right direction or a left-turn stimulus for stimulating turning to a left direction when the angular difference determined by the processing unit is greater than a pre-defined threshold,
   wherein the one or the combination of the displacement, the velocity or the acceleration of the electronic backpack of the locomotion stimulation device monitored by the positioning component is a corresponding one or a combination of an angular displacement, an angular velocity or an angular acceleration of the electronic backpack of the locomotion stimulation device, and wherein the pre-defined minimum displacement, the pre-defined minimum velocity or the pre-defined minimum acceleration is a pre-defined minimum angular displacement, a pre-defined minimum angular velocity or a pre-defined minimum angular acceleration.

15. The system as claimed in claim 12, wherein the positioning unit of the electronic backpack of the locomotion device is configured to resume monitoring of the position and the orientation of the electronic backpack of the locomotion stimulation device after the stimulator of the electronic backpack of the locomotion device ceases providing the stimulus to the animal for a predetermined period of time.

16. The system as claimed in claim 14, wherein, in response to the corresponding one or the combination of the displacement, the velocity or the acceleration of the motion of the hybrid robot being below the pre-defined minimum displacement, the pre-defined minimum velocity or the pre-defined minimum acceleration respectively, the stimulator of the electronic backpack of the locomotion stimulation device is further configured to provide an acceleration stimulus for a first predetermined period of time to induce acceleration of the animal after ceasing provision of the right-turn stimulus or left-turn stimulus to the animal, and to cease provision of the acceleration stimulus for a second predetermined period of time to the animal after the first predetermined period of time of providing the acceleration stimulus, and wherein the positioning unit of the electronic backpack of the locomotion device is configured to resume monitoring of the position and the orientation of the electronic backpack of the locomotion stimulation device after the stimulator of the electronic backpack of the locomotion device ceases providing the acceleration stimulus to the animal for the second predetermined period of time.

17. The system as claimed in claim 12, wherein the processing unit of the animal locomotion control system is configured to send a stimulation control signal to the electronic backpack of the locomotion control device based on the angular difference determined so as to control the stimulator of the electronic backpack of the locomotion stimulation device to provide the stimulus to the animal.

18. The system as claimed in claim 16, wherein the processing unit of the animal locomotion control system is configured to compare the one or the combination of the displacement, the velocity or the acceleration of the electronic backpack of the locomotion stimulation device with the pre-defined minimum displacement, the pre-defined minimum velocity or the pre-defined minimum acceleration respectively and send a cease-stimulation control signal to the stimulator of the electronic backpack of the locomotion stimulation device when the one or the combination of the displacement, the velocity or the acceleration of the electronic backpack of the locomotion stimulation device is less than the pre-defined minimum displacement, the pre-defined minimum velocity or the pre-defined minimum acceleration respectively.

19. The system as claimed in claim 18, wherein the processing unit of the animal locomotion control system is configured to send an acceleration stimulation control signal to the stimulator of the electronic backpack of the locomotion stimulation device after sending the cease-stimulation control signal,
   wherein the processing unit of the animal locomotion control system is configured to send a cease-acceleration stimulation control signal to the stimulator of the electronic backpack of the locomotion stimulation device after the first predetermined period of time.

20. The system as claimed in claim 12, wherein the stimulator of the electronic backpack comprises an electric stimulator,
   wherein the electric stimulator of the electronic backpack comprises a voltage source to generate a voltage waveform output signal to be transmitted to the at least one electrode.

* * * * *

UNITED STATES PATENT AND TRADEMARK OFFICE
CERTIFICATE OF CORRECTION

| | | |
|---|---|---|
| PATENT NO. | : 12,420,090 B2 | Page 1 of 1 |
| APPLICATION NO. | : 17/780952 | |
| DATED | : September 23, 2025 | |
| INVENTOR(S) | : Hirotaka Sato et al. | |

It is certified that error appears in the above-identified patent and that said Letters Patent is hereby corrected as shown below:

In the Claims

<u>Column 38, Claim 1, Line 8:</u>
"manner-se as to allow" should read: -- manner to allow --.

Signed and Sealed this
Ninth Day of December, 2025

John A. Squires
*Director of the United States Patent and Trademark Office*